US010472668B2

(12) United States Patent
Abravaya et al.

(10) Patent No.: US 10,472,668 B2
(45) Date of Patent: Nov. 12, 2019

(54) DOUBLE STRANDED LINEAR NUCLEIC ACID PROBE

(71) Applicant: Abbott Molecular Inc., Des Plaines, IL (US)

(72) Inventors: Klara X. Abravaya, Kenilworth, IL (US); John R. Hackett, Libertyville, IL (US); Shihai X. Huang, Lincolnshire, IL (US); Ka-Cheung X. Luk, Lake Bluff, IL (US); John A. Salituro, Union Grove, WI (US); Larry E. Morrison, Oro Valley, AZ (US)

(73) Assignee: Abbott Molecular Inc., Des Plaines, IL (US)

( * ) Notice: Subject to any disclaimer, the term of this patent is extended or adjusted under 35 U.S.C. 154(b) by 317 days.

(21) Appl. No.: 15/180,357

(22) Filed: Jun. 13, 2016

(65) Prior Publication Data

US 2016/0289749 A1    Oct. 6, 2016

Related U.S. Application Data

(63) Continuation of application No. 14/036,527, filed on Sep. 25, 2013, now Pat. No. 9,388,455, which is a continuation of application No. 10/999,760, filed on Nov. 30, 2004, now abandoned.

(60) Provisional application No. 60/526,480, filed on Dec. 3, 2003.

(51) Int. Cl.
  *C12Q 1/68* (2018.01)
  *C12Q 1/6818* (2018.01)
  *C12Q 1/6832* (2018.01)
  *C12Q 1/6851* (2018.01)

(52) U.S. Cl.
  CPC ......... *C12Q 1/6818* (2013.01); *C12Q 1/6832* (2013.01); *C12Q 1/6851* (2013.01)

(58) Field of Classification Search
  None
  See application file for complete search history.

(56) References Cited

U.S. PATENT DOCUMENTS

| 4,988,617 A | 1/1991 | Landegren et al. |
| 5,565,322 A | 10/1996 | Heller |
| 5,846,726 A | 12/1998 | Nadeau et al. |
| 5,928,869 A | 7/1999 | Nadeau et al. |
| 6,030,787 A | 2/2000 | Livak et al. |
| 6,103,476 A | 8/2000 | Tyagi et al. |
| 6,165,737 A | 12/2000 | Wang et al. |
| 6,258,569 B1 | 7/2001 | Livak et al. |
| 6,458,527 B1 | 10/2002 | Luciw et al. |
| 6,607,889 B1 | 8/2003 | Coull et al. |

FOREIGN PATENT DOCUMENTS

| EP | 0909823 A2 | 4/1999 |
| EP | 0861906 B1 | 3/2006 |
| WO | 9729210 | 8/1997 |
| WO | 9732044 A1 | 9/1997 |
| WO | 9746707 A2 | 12/1997 |
| WO | 9949293 | 9/1999 |
| WO | 0230946 A1 | 4/2002 |

OTHER PUBLICATIONS

Genbank GI:22532281 [online] Aug. 28, 2002 [retrieved on May 27, 2009] retrieved from: http://www.ncbi.nlm.nih.gov/nuccore/22532281.
Tyagi S. and Kramer F.R., Nature Biotechnology, vol. 14, pp. 303-308 (1996).
Piatek, et al., Nature Biotechnology, vol. 16, pp. 359-363 (1998).
Marras S. et al., Genetic Analysis: Biomolecular Engineering, vol. 14, pp. 151-156 (1999).
Tapp I. et al., BioTechniques, vol. 28, pp. 732-738 (2000).
Lee L.G. et al., Nucleic Acids Research, vol. 21, pp. 3761-3766 (1993).
Morrison L. et al., Anal. Biochem., vol. 183, pp. 231-244 (1989).
Li et al., Nucleic Acids Research, vol. 30, No. 2, e5 (2002).
Nielsen et al., Science, vol. 254, pp. 1497-1500 (1991).

*Primary Examiner* — Samuel C Woolwine
(74) *Attorney, Agent, or Firm* — Pierce Atwood LLP; Kevin M. Farrell

(57) ABSTRACT

A double-stranded nucleic acid hybridization probe and methods of using the same are described. The probe described is particularly suited for real-time RT-PCR reactions and has high tolerance to mismatches.

8 Claims, 18 Drawing Sheets

Specification includes a Sequence Listing.

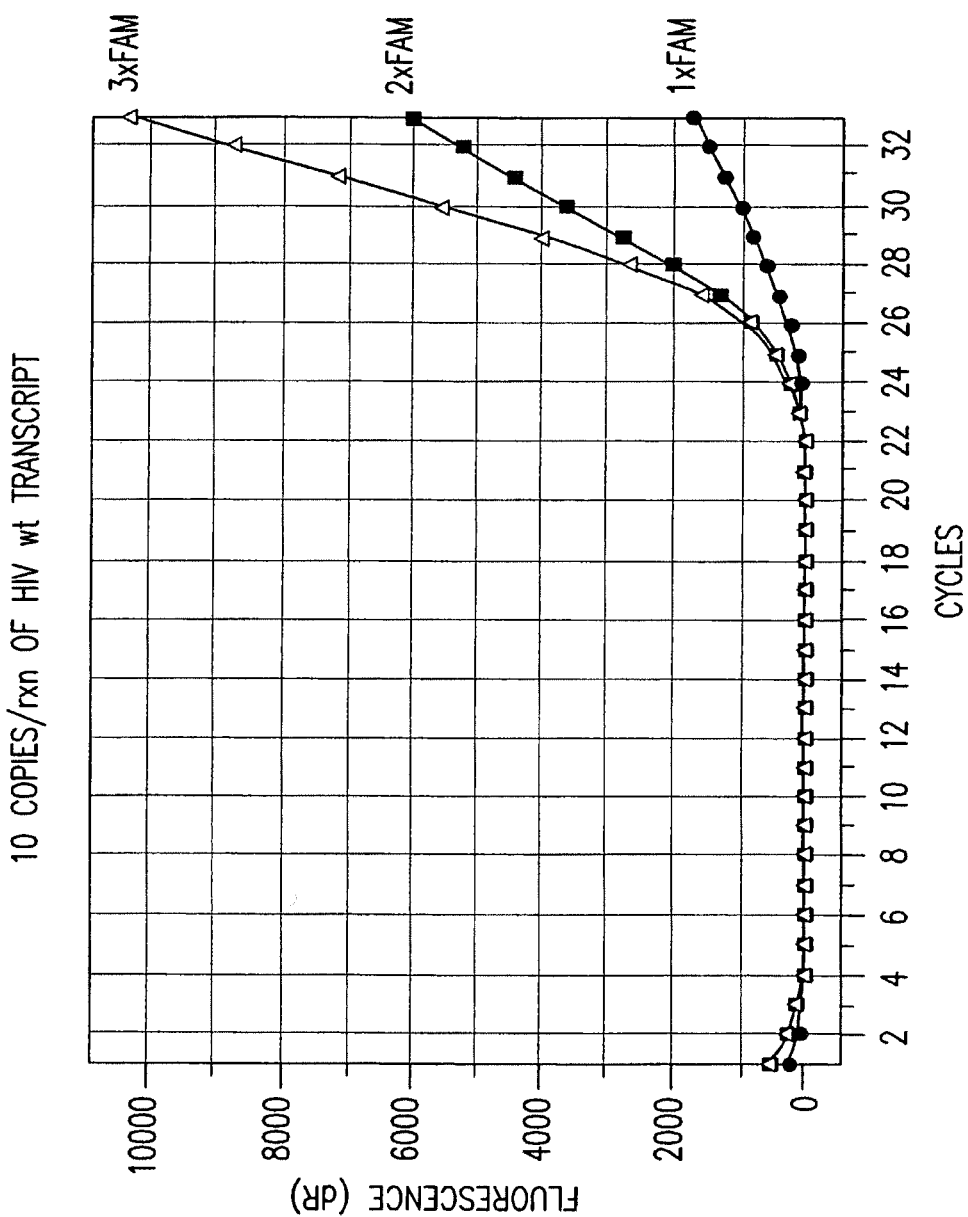

SEQUENCE LISTING

<160> NUMBER OF SEQ ID NOS: 16

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
attccctaca atccccaaag tcaaggagt                                      29

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cccctgcact gtaccccca atccc                                           25

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cccctgcact gtaccccca atcc                                            24

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-6-FAM
<220> FEATURE:
<223> OTHER INFORMATION: 3'-DABCYL

<400> SEQUENCE: 4
acagcagtac aaatggcagt                                                20

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-6-FAM
<220> FEATURE:
<223> OTHER INFORMATION: 3'-DABCYL

<400> SEQUENCE: 5
acagcagtac aaatggcagt attcatccac a                                   31

<210> SEQ ID NO 6
<211> LENGTH: 41
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-6-FAM
<220> FEATURE:
<223> OTHER INFORMATION: 3'-DABCYL

<400> SEQUENCE: 6
gctacagcag tacaaatggc agtattcatc cacaatttcc c                        41

<210> SEQ ID NO 7
<211> LENGTH: 47
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-6-FAM
<220> FEATURE:
<223> OTHER INFORMATION: 3'-DABCYL

<400> SEQUENCE: 7
gcacagcagt acaaatggca gtattcatcc acaattttaa aagaaaa        47

<210> SEQ ID NO 8
<211> LENGTH: 50
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-6-FAM
<220> FEATURE:
<223> OTHER INFORMATION: 3'-6-FAM

<400> SEQUENCE: 8
gcacagcagt acaaatggca gtattcatcc acaattttaa aagaaaacgc        50

<210> SEQ ID NO 9
<211> LENGTH: 50
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-6-FAM
<220> FEATURE:
<221> NAME/KEY: modified_base
<222> LOCATION: (36)..(36)
<223> OTHER INFORMATION: dT-6-FAM
<220> FEATURE:
<223> OTHER INFORMATION: 3'-6-FAM

<400> SEQUENCE: 9
gcacagcagt acaaatggca gtattcatcc acaattttaa aagaaaacgc        50

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence: Synthetic
      quenching oligonucleotide
<220> FEATURE:
<223> OTHER INFORMATION: 3'-DABCYL

<400> SEQUENCE: 10
gtattgtact gctgt        15

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Synthetic
      quenching oligonucleotide
<220> FEATURE:
<223> OTHER INFORMATION: 3'-DABCYL

<400> SEQUENCE: 11
cggatttgta ctgctgt        17

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      quenching oligonucleotide
<220> FEATURE:

```
<223> OTHER INFORMATION: 3'-DABCYL

<400> SEQUENCE: 12
gacccatttg tactgctgt                                                19

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      quenching oligonucleotide
<220> FEATURE:
<223> OTHER INFORMATION: 5'-DABCYL
<220> FEATURE:
<223> OTHER INFORMATION: 3'-DABCYL

<400> SEQUENCE: 13
gacccatttg tactgctgta gc                                            22

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      quenching oligonucleotide
<220> FEATURE:
<223> OTHER INFORMATION: 5'-DABCYL
<220> FEATURE:
<223> OTHER INFORMATION: 3'-DABCYL

<400> SEQUENCE: 14
tgagccattt gtactgctgt agc                                           23

<210> SEQ ID NO 15
<211> LENGTH: 15
<212> TYPE: DNA
<213> ORGANISM: Artificial Sequence
<220> FEATURE:
<223> OTHER INFORMATION: Description of Artificial Sequence: Synthetic
      quenching oligonucleotide
<220> FEATURE:
<223> OTHER INFORMATION: 3'-BHQ-1

<400> SEQUENCE: 15
tttgtactgc tgtgc                                                    15

<210> SEQ ID NO 16
<211> LENGTH: 15
<212> TYPE: DNA
<213> ORGANISM: Artificial Sequence
<220> FEATURE:
<223> OTHER INFORMATION: Description of Artificial Sequence: Synthetic
      quenching oligonucleotide
<220> FEATURE:
<223> OTHER INFORMATION: 5'-BHQ-1
<220> FEATURE:
<223> OTHER INFORMATION: 3'-BHQ-1

<400> SEQUENCE: 16
gcgttttctt ttaaa                                                    15
```

DOUBLE STRANDED LINEAR NUCLEIC ACID PROBE

FIELD OF INVENTION

The invention relates generally to the field of nucleic acid amplification and detection. Additionally, the invention relates to compositions and methods for performing PCR and probe hybridization using a single reagent mixture.

BACKGROUND

DNA-based analyses are used routinely in a wide spectrum of settings, including clinical hematology, molecular genetics, microbiology and immunology. Many current techniques rely on PCR amplification of a polynucleotide of interest (hereinafter "target molecule") in conjunction with several types of post-amplification detection techniques. Other non-PCR based amplification techniques are well known in the art including, but not limited to, oligo ligation assay (OLA), ligase chain reaction (LCR), transcription-mediated amplification (TMA), and strand displacement amplification (SDA). Additionally, these techniques are amenable to mixing. That is, the product of one amplification reaction can be used as the target of another amplification reaction, which allows great sensitivity with an additional step that tends to increase sensitivity.

One preferred amplification format is known as a real-time homogeneous assay. A real-time assay is one that produces data indicative of the presence or quantity of a target molecule during the amplification process, as opposed to the end of the amplification process. A homogeneous assay is one in which the amplification and detection reagents are mixed together and simultaneously contacted with a sample, which may contain a target nucleic acid molecule. Thus, the ability to detect and quantify DNA targets in real-time homogeneous systems as amplification proceeds is centered in single-tube assays in which the processes required for target molecule amplification and detection take place in a single "close-tube" reaction format. For example, current techniques that use PCR amplification and have these features are generally known as Real-Time PCR techniques. Similarly, non-PCR-based technologies are also within the skill of the ordinary artisan and are amenable to homogeneous detection methods.

In most amplification and detection techniques a probe is used to detect an amplification product. Several probe systems known in the art utilize a fluorophore and quencher. For example, molecular beacon probes are single-stranded oligonucleic acid probes that can form a hairpin structure in which a fluorophore and a quencher are usually placed on the opposite ends of the oligonucleotide. At either end of the probe short complementary sequences allow for the formation of an intramolecular stem, which enables the fluorophore and the quencher to come into close proximity. The loop portion of the molecular beacon is complementary to a target nucleic acid of interest. Binding of this probe to its target nucleic acid of interest forms a hybrid that forces the stem apart. This causes a conformation change that moves the fluorophore and the quencher away from each other and leads to a more intense fluorescent signal. Molecular beacon probes are, however, highly sensitive to small sequence variation in the probe target (Tyagi S. and Kramer F. R., *Nature Biotechnology, Vol.* 14, pages 303-308 (1996); Tyagi et al., *Nature Biotechnology, Vol.* 16, pages 49-53(1998); Piatek et al., *Nature Biotechnology, Vol.* 16 pages 359-363 (1998); Marras S. et al., *Genetic Analysis: Biomolecular Engineering, Vol.* 14, pages 151-156 (1999); Tapp I. et al, *BioTechniques, Vol* 28, pages 732-738 (2000)).

Unlike molecular beacon probes, some single-stranded linear probes possessing also a quencher and a fluorophore attached at opposite ends of an oligonucleotide do not form a hairpin structure. Instead, this kind of linear oligonucleotide probes in solution behaves like a random coil, its two ends occasionally come close to one another, resulting in a measurable change in energy transfer. However, when the probe binds to its target, the probe-target hybrid forces the two ends of the probe apart, disrupting the interaction between the two terminal moieties, and thus restoring the fluorescent signal from the fluorophore. In addition, single-stranded linear probes can be designed as "TaqMan probes", that bind to target strands during PCR and thus can be enzymatically cleaved by the 5'→3' exonuclease activity of the Taq DNA polymerase during the primer extension phase of the PCR cycle resulting in an increase in fluorescence in each cycle proportional to the amount of specific product generated. It has been reported that long single-stranded linear probes suffer from high "background" signals, while shorter ones are sensitive to single-base mismatches (Lee L. G. et al., *Nucleic Acids Research, Vol.* 21, pages 3761-3766 (1993); Täpp I. et al. (above); U.S. Pat. Nos. 6,258,569; 6,030,787).

Double-stranded linear probes are also known in the art. Double-stranded linear probes have two complementary oligonucleotides. The probes described in the prior art have been of equal length, in which at least one of the oligonucleotides acts as a probe for a target sequence in a single-stranded conformation. The 5' end of one of the oligonucleotides is labeled with a fluorophore and the 3' end of the other oligonucleotide is labeled with a quencher, e.g., an acceptor fluorophore, or vice versa. When these two oligonucleotides are annealed to each other, the two labels are close to one another, thereby quenching fluorescence. Target nucleic acids, however, compete for binding to the probe, resulting in a less than proportional increase of probe fluorescence with increasing target nucleic acid concentration (Morrison L. et al., *Anal. Biochem., Vol.* 183, pages 231-244 (1989); U.S. Pat. No. 5,928,862).

Double-stranded linear probes modified by shortening one of the two complementary oligonucleotides by few bases to make a partially double-stranded linear probe, are also known in the art. In such double-stranded linear probes in the prior art, the longer oligonucleotide has been end-labeled with a fluorophore and the slightly shorter oligonucleotide has been end-labeled with a quencher. In the double-stranded form, the probe is less fluorescent due to the close proximity of the fluorophore and the quencher. In the presence of a target, however, the shorter quencher oligonucleotide is displaced by the target. As a result, the longer oligonucleotide (in the form of probe-target hybrid) becomes substantially more fluorescent.

The double-stranded probes known in the prior art having oligonucleotides of unequal lengths display complete discrimination between a perfectly matched target and single nucleotide mismatch targets. Also, these probes do not have optimal reaction kinetics especially when low quantities of target nucleic acid are present. (Li et al., *Nucleic Acids Research, Vol.* 30, No. 2, e5 (2002))

The detection of viral RNAs presents certain challenges, which are not presented by the desire to detect DNAs of interest. The probes of the prior art are suitable for the detection of viral RNAs, but could be improved. First, some viral RNA targets are prone to rapid mutation in the bodies of their hosts. To ensure that mutated viral RNA sequences are detected along with so-called "wild-type" sequences, nucleic acid probes used to detect viral RNAs should be tolerant of mismatches, yet still specific enough to avoid interaction with non-target nucleic acids. (i.e., false-positive results). Many of the probes of the prior art are sensitive to single-nucleotide changes, and therefore, are not optimal for the detection of viral nucleic acids.

Additionally, viral RNAs often must be reverse transcribed into DNA before amplification of a nucleic acid sequence of interest. Unfortunately, it has been discovered by the present inventors that some prior art nucleic acid probes can interfere with the reverse transcription (i.e., enzymatic copying of RNA sequences into DNA sequences).

It is also desirable that nucleic acid probes be capable of sensitively detecting both small and large quantities of nucleic acids of interest. Some nucleic acids probes of the prior art are not well suited to detecting small quantity of nucleic acids of interest. Other nucleic acids probes of the prior art are not well suited to the sensitive detection of large quantities of nucleic acids.

In view of the above, there is a need for a probe in which: a) the sequences can be readily manipulated, b) the oligonucleotides are easy to design without the limitation of being capable of forming stem or loop, c) there is high tolerance to mismatches, and/or d) the oligonucleotides are suitable for real-time RT-PCR reactions.

SUMMARY OF THE INVENTION

The present invention relates generally to double-stranded nucleic acid hybridization probes and methods of using the same. The probe of the present application can be used in any suitable manner, and is particularly well suited for PCR amplification and probe hybridization using a single reaction vessel and a single reagent mixture.

The present invention provides a nucleic acid probe that comprises a first oligonucleic acid and a second oligonucleic acid. The first oligonucleic acid is labeled by a fluorophore and is substantially complementary to a nucleic acid of interest, such that when the nucleic acid of interest is present, the first oligonucleic acid can bind to the nucleic acid of interest. The second oligonucleic acid has a quencher molecule and is substantially complementary to the first oligonucleic acid. Accordingly, the first and second oligonucleic acids can bind together to form a double-stranded nucleic acid. When the first oligonucleic acid is bound to the second oligonucleic acid, the fluorescent emission of the fluorophore attached to the first oligonucleic acid is quenched (i.e., detectably less than the emission of the same fluorophore when the first oligonucleic acid and second oligonucleic acid are not bound together). Binding of the first oligonucleic acid to the nucleic acid of interest, therefore, increases the fluorescence in a test system, thereby indicating whether the nucleic acid of interest is present. The first oligonucleic acid comprises "m" contiguous nucleobases substantially complementary to a nucleic acid of interest, and the second oligonucleic acid comprises "n" contiguous nucleobases substantially complementary to the first oligonucleic acid, wherein "m" and "n" are independently selected integers, and when m is less than 25, n is up to one half of m; when m is 26 to 29, n is from 8 to 13; when m is 30 to 34, n is from 8 to 15; when m is 35 to 39, n is from 8 to 20; when m is 40 to 44, n is 9 to 25; when m is 45 to 49, n is 10 to 30; when m is 50 to 54, n is 10 to 35; when m is 55 to 59, n is 10 to 40; when m is 60 to 64, n is 11 to 45; when m is 65 to 69, n is from 11 to 50; when m is 70 to 75, n is from 15 to 55.

The present invention also provides a nucleic acid probe in which the first and longer oligonucleic acid is substantially complementary to a nucleic acid of interest and comprises a quencher. The second, and shorter, oligonucleic acid comprises a fluorophore. The first oligonucleic acid is substantially complementary to the second oligonucleic acid, which permits simultaneous hybridization of the first oligonucleic acid with the second oligonucleic acid, and quenching of the fluorescence of the second oligonucleic acid. When the first oligonucleic acid is bound to a nucleic acid of interest, the second oligonucleic acid is displaced and the fluorescent emission of the fluorophore is detectably greater than when it is annealed to the first oligonucleic acid.

The present invention also provides a method of detecting or quantifying a nucleic acid of interest in a test sample using any embodiment of the nucleic acid probe of the present invention described herein. For example, the present invention provides a method of quantifying RNA in a test sample in which the sample is contacted with nucleic acid amplification reagents and reverse transcription reagents under conditions permissive of reverse transcription, and then/also of nucleic acid amplification such that cDNA is produced and amplified. The mixture is subsequently or simultaneously contacted with a nucleic acid probe of the present invention as described herein, wherein the first and second oligonucleic acids of the probe do not bind together and/or to the target RNA, at the temperature of the reverse transcription step.

The present invention also provides a method of detecting and/or quantifying a nucleic acid of interest in a test sample in which the sample is contacted with DNA amplification reagents to amplify a portion of the nucleic acid of interest, and a first oligonucleic acid probe that has a fluorophore and a quencher, and is specific for the amplified nucleic acid. Before, during or after the addition of the first single-stranded oligonucleic acid, a second oligonucleic acid comprising a quencher is added in a ratio so that the second to the first oligonucleic acids in the mixture can be less than one, and so that the first and second oligonucleic acids form a duplex in solution.

DESCRIPTION OF THE DRAWINGS

FIG. 5A-D graphically presents real-time RT-PCR amplification plot data of wild type transcript detected by the 1×FAM probe (slin-47), the 2×FAM probe (dfam-50) or the 3×FAM probe (fam-650) (as indicated next to each curve) at the transcript copy number of 10 copies (A), 10e3 copies (B), 10e5 copies (C) or 10e6 copies (D) per PCR reaction. Each of the three PAM-labeled linear oligonucleic acid probes was quenched by oligos sque-15BH and bhq-5015.

DETAILED DESCRIPTION

Figure 1A:
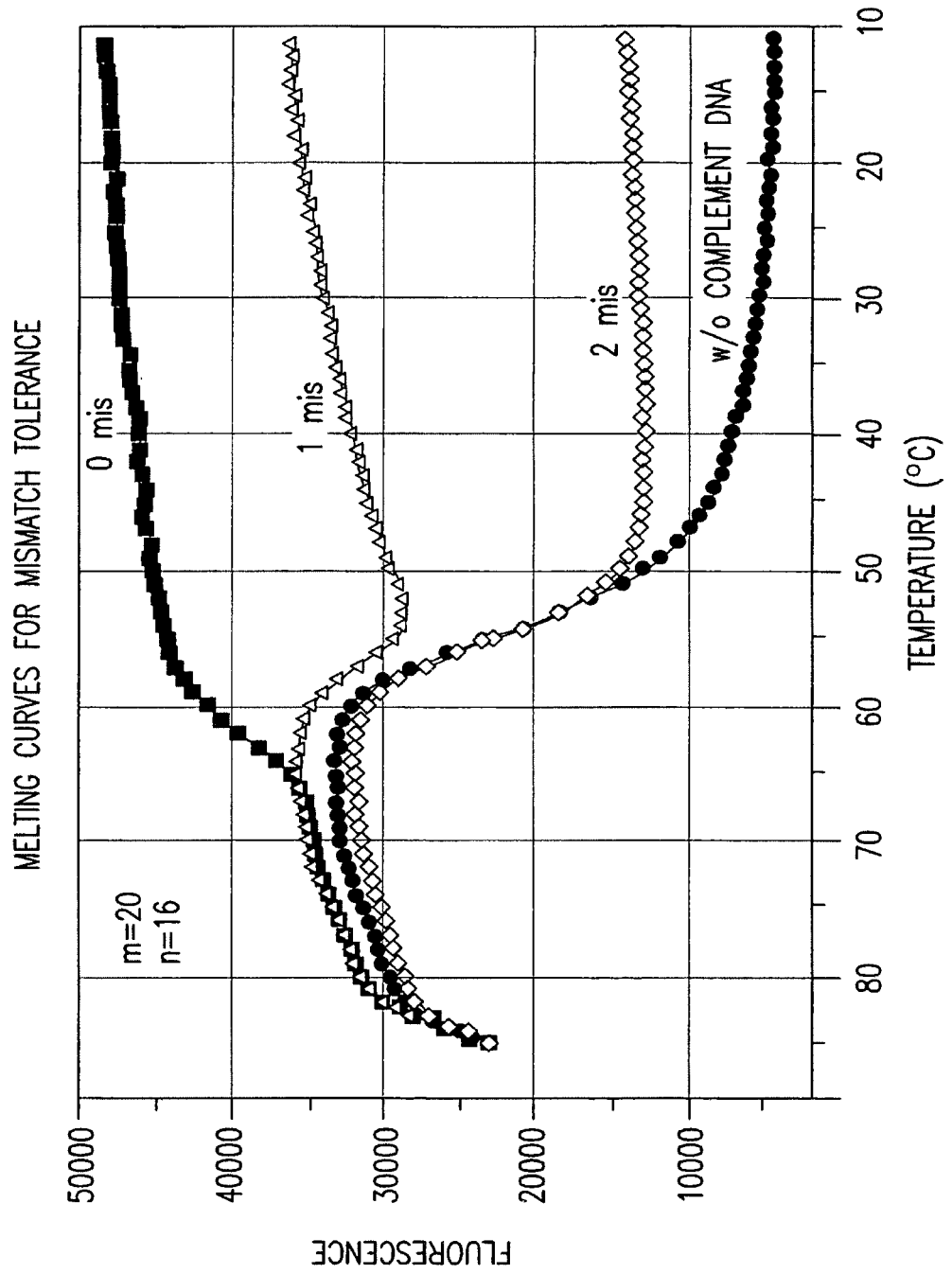
FIG. 1A-F graphically presents melting curve data of nucleic acid probes of the present invention without or with mismatched target oligonucleotides (as denoted next to each curve). (A) 520-20/que-16; (B) 520-20/que-14; (C) 520-20/que-12; (D) 520-31/que-14; (E) 520-20/que-12; (F) 520-31/que-14. "m" indicates the length of the contiguous nucleobases of the FAM-labeled oligonucleic acid substantially complementary to the target, whereas "n" represents the length of the contiguous nucleobases of the DABCYL-labeled quenching oligonucleic acid substantially complementary to the FAM-labeled oligonucleic acid.

The present invention provides nucleic acid probes as described below useful to detect the presence of a nucleic acid of interest (also commonly called a target). Of course, the first oligonucleic acid can also bind to amplified portions of the nucleic acid of interest. For ease of description and understanding, references to nucleic acids of interest or "targets" refer both to these moieties as found in a test sample and to amplified copies of portions of these nucleic acids, unless specifically noted to the contrary.

The present invention provides a nucleic acid probe that comprises a first oligonucleic acid and a second oligonucleic acid. The first oligonucleic acid is labeled by a fluorophore and is substantially complementary to a nucleic acid of interest, such that when the nucleic acid of interest is present, the first oligonucleic acid can bind to the nucleic acid of interest. For purposes of the present invention, the term "substantially complementary" means that equal or more than 80% of nucleobases on one strand of the probe finds its Watson-Crick binding partner on the other strand of the probe (or in the nucleic acid of interest) in an alignment such that the corresponding nucleotides can hybridize to each other. Binding of the first oligonucleic acid to the nucleic acid of interest prevents the second oligonucleic acid from binding to the first oligonucleic acid of the probe. The second oligonucleic acid has a quencher molecule and is also substantially complementary to the first oligonucleic acid. Accordingly, the first and second oligonucleic acids can bind together when the nucleic acid of interest is not present to form a double-stranded nucleic acid. When the first oligonucleic acid is bound with the second oligonucleic acid, the fluorescent emission of the fluorophore attached to the first oligonucleic acid is quenched (i.e., detectably changed, and preferably lessened, compared to the emission of the same fluorophore when the first oligonucleic acid and second oligonucleic acid are not bound together). Binding of the first oligonucleic acid to the nucleic acid of interest, therefore, changes and preferably increases the fluorescence in a test system, thereby indicating whether the nucleic acid of interest is present. In one embodiment, the first oligonucleic acid contains 15-75 nucleobases ("m") substantially complementary to target, and the second oligonucleic acid contains "n" nucleobases substantially complementary to the first oligonucleic acid, whereas "n" is significantly shorter than "m". The second oligonucleic acid can be of any suitable length with the primary consideration being that when the nucleic acid of interest is not present, the second oligonucleic acid must bind with the first oligonucleic acid under temperature and solvent conditions in which the probe will be used to infer the presence or absence of the nucleic acid of interest in a test sample.

Table 1 sets forth preferred and more preferred lengths of the first and second oligonucleic acids incorporated into two-stranded probes of this embodiment of the present invention

TABLE 1

| First Oligonucleic Acid* | Second Oligonucleic Acid** | |
|---|---|---|
|  | Preferred | More Preferred |
| <25 | <13 | 6-10 |
| 25-30 | 8-13 | 8-10 |
| 31-34 | 8-15 | 10-14 |
| 35-39 | 8-20 | 12-18 |
| 40-44 | 9-25 | 12-22 |
| 45-49 | 10-30 | 15-28 |
| 50-54 | 10-35 | 25-32 |
| 55-59 | 10-40 | 28-35 |
| 60-64 | 11-45 | 30-40 |
| 65-69 | 11-50 | 35-45 |
| 70-75 | 15-55 | 48-50 |

*Length in nucleobases ("m") substantially complementary to target.
**Length in nucleobases ("n") substantially complementary to first oligonucleic acid.

While not desiring to be bound by any particular theory, it is believed that the long single strand portion of the first oligonucleic acid strongly favors binding of the first oligonucleic acid to the target nucleic acid of interest thereby increasing the sensitivity of the probe and under some conditions improving the kinetics of the detection reaction. Additionally, the longer length of the first oligonucleic acid allows the use of hybridization conditions that permit mismatch hybridization.

Oligonucleic acids are oligomers of naturally occurring or modified nucleobases. While guanine, adenine, thymine, uridine, cytosine, and optionally inosine and/or indole, are among the preferred nucleobases incorporated in the oligonucleic acids of the present invention, any suitable nucleobase can be incorporated into the probes of the present invention. Oligonucleic acids are not necessarily acids or residues of acids. Rather an oligonucleic acid as used herein is a polymer of nucleobases or nucleobase analogs that are capable of specifically binding to a target polynucleotide by way of a regular pattern of monomer-to-monomer interactions, such as Watson-Crick type of base pairing, or the like. Most commonly, the monomers are linked by phosphodiester bonds. Less commonly, the monomers are linked by analogs of phosphodiester bonds, such as (deoxyribosyl) phosphonyl polymers or phosphothiorate polymers. Also less commonly employed are peptide nucleic acids, commonly referred to in the art as PNAs, in which the nucleobases are linked in sequence by a polymer containing amide bonds at regular intervals (Nielsen et al., *Science*, Vol. 254: 1497-1500 (1991)).

Methods of synthesizing oligonucleic acids incorporated into probes of the present invention are well known in the art and any suitable method of obtaining the oligonucleic acids of the present invention can be used.

A fluorophore, or a "fluorescent label", can be any suitable moiety capable of emitting light. The light can be generated chemically, biologically, in response to excitational photons, or from any other suitable cause. Preferably, fluorophores are fluorescent organic dyes derivatized for attachment to the oligonucleic acids of the probe via a linking moiety. When ribosyl or deoxyribosyl polymers are used to link the nucleobases together the dyes can advantageously be derivatized to link to the terminal 3' carbon or terminal 5' carbon of the polymer.

Fluorophores suitable in the context of the present invention include (without limitation) the Violet/Blue dyes ($Em_{max}$ 375-491 nm) 7-methoxycoumarin-3-carboxy, AMCA-X (7-aminocoumarin-X), 6-MI or 6-MAP (6-methyl-8-(2-deoy-β-D-ribofuranosyl)isoxanthopteridine); the Green/Yellow dyes ($Em_{max}$ 492-585 nm) DTAF (4,6-dichlorotriazinyl)aminofluorescein, 6-FAM (fluorescein, 6-carboxyfluorescein), Dansyl-X (6-((5-dimethtylaminonaphtalene-1-sulfonyl)amino)hexanoate, 6-JOE (6-carboxy-4',5'-dichloro-2',7'-dimethoxyfluorescein), HEX (hexachlorofluorescein), BODIPY-TMR-X (tetramethylrhodamine substitute), PyMPO (1-(3-carboxybenzyl)-4-(5-(4-methoxyphenyl)oxazol-2-yl)pyridinium bromide), TAMRA-X (6-(tetramethylrhodamine-5(6)-carboxamido)hexanoate); the Orange dyes ($Em_{max}$ 586-647 nm) rhodamine derivatives BODIPY 576/589, BODIPY 581/591, ROX (carboxyrhodamine), VIC (Applied Biosystems Inc., Foster City, Calif.), NED (Applied Biosystems Inc., Foster City, Calif.) and the Red dyes ($E_{max}$ 647-700 nm) as carboxynaphthofluorescein.

A quencher as used herein is a moiety that decreases the light emitted by the fluorophore at the wavelength at which signal is measured, or is a fluorescent moiety that serves to shift the wavelength of light emitted by the fluorophore of the nucleic acid probe. Quenchers suitable in the context of the present invention include (without limitation) DABCYL (4-(4'-dimethylaminophenylazo)benzoic acid), QSY-7 (9-[2-[[4-[[(2,5-dioxo-1-pyrrolidinyl)oxy]carbonyl]-1-piperidinyl]sulfonyl]phenyl]-3,6-bis(methylphenylamino)), BHQ-1, BHQ-2, BHQ-3 (Biosearch Technologies Inc., 2003, Cat. Nos. BG5-5041T, BG5-5042T, and BG5-5043T) and TAMRA ((6-tetramethylrhodamine-5(6)-carboxamido) hexanoate). Additionally, a quencher can be an organic dye, which may or may not be fluorescent, depending on the embodiment of the invention.

In yet another embodiment, the present invention comprises a probe wherein the first and second oligonucleic acids comprise additional nucleobases that are not complementary to the nucleic acid of interest or to the first nucleic acid, respectively, at the 5' or the 3' end.

In another embodiment the present invention comprises a probe wherein the ratio of the second oligonucleic acid comprising the quencher to the first oligonucleic acid comprising the fluorophore may be more than 1.1. Additionally, another embodiment comprises a probe in which the ratio of the second oligonucleic acid comprising the quencher to the first oligonucleic acid comprising the fluorophore may be more than 0.1 and less than 0.9.

In another embodiment of the present inventive probe the first oligonucleic acid comprises two label moieties, one fluorophore and one quencher. The incorporation of a quencher (in addition to the fluorophore) in the first oligonucleic acid reduces background fluorescent emission (or background signal) that would occur when first oligonucleic acid is bound neither to target, nor to a second oligonucleic acid comprising a quencher. Another embodiment comprises a probe in which the molar ratio of the second oligonucleic acid (comprising a quencher) to the first oligonucleic acid (comprising one fluorophore and one quencher) is more than 0.1 and less than 0.9. Additionally, another embodiment comprises a probe in which the molar ratio of the second oligonucleic acid to the first oligonucleic acid (with two label moieties) is more than 1.1.

To improve the fluorescent signal from the nucleic acid probe of the present invention, more than one fluorophore may be linked to the oligonucleic acid that binds to the target. Probes of the present invention comprising more than one fluorophore preferably emit substantially more fluorescent signal than equivalent probes comprising only a single fluorophore. Unexpectedly, the probes containing at least three fluorophores have been found to be tolerant of mismatches (i.e., less than perfect complementarity) with target molecules. This can be especially advantageous when the target nucleic acid is highly polymorphic as is the case with portions of HIV-1 and other retroviruses. Because the mismatch tolerance of the probes of the present invention is independent of the number of fluorophores attached to the first oligonucleic acid of the probe, and a probe with more than one fluorophore shows the same high tolerance for targets with 2, 3 or 4 mismatches as a probe of similar length with only one fluorophore, the probes of the present invention are particularly well suited to the detection and quantitation of viral target sequences.

In another embodiment, the nucleic acid probe of the present invention comprises three oligonucleic acids, the first oligonucleic acid comprises a fluorophore and the second comprises a quencher. The third oligonucleic acid preferably also comprises a quencher. While not desiring to be bound by any particular theory, it is believed that the incorporation of an additional quencher in the third oligonucleic acid reduces background fluorescent emission (or background signal). Generally, background signal is the emission of fluorescence that is not caused by binding of a fluorescently labeled oligonucleic acid of the probe to a target nucleic acid of interest.

In another embodiment, the longer oligonucleic acid comprises a quencher and the shorter oligonucleic acid comprises a fluorophore. Additionally, this embodiment comprises a probe in which the first and the second oligonucleotides further comprise additional nucleobases that are not complementary to the nucleic acid of interest and the first oligonucleotide, respectively, at the 5' and 3' ends. Additionally, both the first and second oligonucleic acids can also comprise a plurality of label moieties. For example, both the first oligonucleic acid and the second oligonucleic acid can comprise both a fluorophore and a quencher. Typically, the fluorophore and the quencher are incorporated into the oligonucleic acids such that when bound to an unlabeled oligonucleotide sequence (e.g., a target) the fluorophore and the quencher are separated and the fluorophore can emit light. However, when the first oligonucleic acid and the second oligonucleic acid of the probe are bound together the fluorophore of the first oligonucleic acid is brought into proximity with the quencher of the second oligonucleic acid, as well as the converse (i.e., the fluorophore of the second oligonucleic acid is brought into proximity with the quencher of the first oligonucleic acid). In this way, both the first and second oligonucleic acids can emit light in the presence of a target, but are mutually quenched in the absence of the target. Furthermore, the first and second oligonucleic acids of this embodiment may comprise additional nucleobases that are not complimentary to the nucleic acid of interest or to the first nucleic acid, respectively, at the 5' or the 3' end.

Additionally, this embodiment comprises a nucleic acid probe wherein the ratio of the first oligonucleic acid comprising the quencher to the second oligonucleic acid comprising the fluorophore is more than 1.1. In yet another embodiment, the first oligonucleic acid comprises an additional quencher. This embodiment allows for a probe in which the ratio of the first oligonucleic acid to the second oligonucleic acid is More than 0.1 and less than 0.9. Also, this embodiment allows for a probe in which the ratio of the first oligonucleic acid to the second oligonucleic acid is more than 1.1.

In a preferred embodiment, the difference in the fluorescence signal between the double stranded form when the fluorophore and quencher are close, and the target-hybridized state when the fluorophore is separated from the quencher can differ by as much as a factor of 20. This effect is due to the fact that when both are in close proximity there is relatively efficient quenching of the fluorophore, whereas, when the first oligonucleic acid is annealed to the target nucleic acid, it is separated from the second oligonucleic acid (comprising a quencher) and the fluorophore is not quenched anymore. As used herein, the terms "quenching" refers to any process whereby when a fluorophore molecule and a quencher molecule are in close proximity, a substantial loss of fluorescence occurs. Including in the group of quenchers are non-fluorescent molecules and fluorescent molecules, which can accept light energy from the fluorophore.

In a preferred embodiment, the 3' terminal of the first oligonucleic acid only, or together with the 3' terminal of the second oligonucleic acid of the probe is/are rendered incapable of extension by a nucleic acid polymerase, to prevent interference with the PCR polymerization step thereby to prevent reduction of the stepwise efficiency of the amplification.

In another embodiment of the present invention, the first oligonucleic acid, or the first and second oligonucleic acids of the double stranded probe are rendered impervious to degradation by the 5'→3' exonuclease activity of a nucleic acid polymerase. Preferably, the 5' end of the oligonucleic acid is rendered resistant to digestion by including one or more modified internucleotide linkages into the 5' end of the oligonucleic acid. Minimally, the 5'-terminal internucleotide linkage must be modified, however, up to all the internucleotide linkages in the oligonucleotide may be modified. Such internucleotide modifications may include modified linkages of the type used in the synthesis of anti-sense oligonucleotides. Examples of such nuclease resistant linkages include peptide nucleic acid (PNA) linkages, e.g., Nielsen et al., *Science*, Vol. 254, pages 1497-1500 (1991), and other like exonuclease resistant linkages. Alternatively, the 5' end can be rendered resistant to degradation by the 5'→3' exonuclease activity by adding a sequence that is not complementary to the nucleic acid of interest, or by the addition of a derivative moiety at the 5' end of the oligonucleic acid.

Advantageously, any of the probes described above, each of which comprise two oligonucleic acids, can be used in a method of determining the presence or quantity of a target nucleic acid. In the following methods, any suitable nucleic acid of interest can be the target nucleic acid. The target nucleic acid, however, is preferably RNA, such as a viral RNA or an mRNA. In some embodiments, the target RNA is preferably reverse transcribed prior to amplification, which amplification is also preferably carried out in the same tube and reaction mixture as the reverse transcription step.

The present inventive method of detecting, or quantifying, a nucleic acid of interest in a test sample comprises mixing test sample with DNA amplification reagents to amplify a portion of the nucleic acid of interest. The reagents can optionally include reverse transcription reagents. The mixture of the amplification reagents and nucleic acid of interest is then incubated under suitable conditions to reverse transcribe the target RNA into a target complementary DNA if applicable, and then to amplify the target DNA. The method also comprises adding a nucleic acid fluorescent probe comprising a first oligonucleic acid with a fluorophore and a second oligonucleic acid with a quencher such as those described above, and measuring fluorescence from the fluorescent probe as an indication of whether the test sample contains the nucleic acid of interest. In some embodiments, the probe is contacted to the nucleic acid of interest before or substantially simultaneously with the amplification reagents, and optionally is mixed with the amplification reagents prior to contacting the amplification reagents to the nucleic acid of interest. In other embodiments, the probe is contacted to the nucleic acid of interest after incubating the nucleic acid of interest and the amplification reagents under suitable amplification conditions (so as to amplify a portion of the nucleic acid of interest).

Amplification reagents refer to the chemicals, apart from the target nucleic acid sequence, needed to perform the PCR process. These chemicals can conveniently be classified into four classes of components: (i) an aqueous buffer, often including without limitation a magnesium salt, (ii) amplification substrates, such as four ribonucleotide triphosphates (NTPs) or preferably at least four deoxyribonucleotide triphosphates (dNTPs) in polymerization-based amplification or ATP in ligation-based amplification, (iii) one or more oligonucleotide primers or probes (normally two primers for each target sequence, the sequences defining the 5' ends of the two complementary strands of the double-stranded target sequence when PCR is employed), and (iv) an amplification enzyme such as a polynucleotide polymerase (for example, Taq polymerase for PCR or RNA polymerase for TMA), or a ligase. Additional reagents or additives can also be included at the discretion of the skilled artisan and selection of these reagents is within the skill of the ordinary artisan. Of course, when the amplification reagents are used to cause both reverse transcription and amplification, then reverse transcription reagents are also included in the amplification reagents. Selection of amplification reagents, according to the method of amplification reaction used, is within the skill of the ordinary artisan.

In embodiments employing "homogeneous" amplification and detection steps, i.e., when performing combined amplification and probe hybridization detection in a single reaction mixture in a single tube, then: (i) any of the two oligonucleic acids of the probe preferably do not block or otherwise interfere or participate in the PCR or other amplification step; (ii) neither oligonucleic acid of the probe is degraded by the enzyme (e.g., by exonuclease activity of a polymerase enzyme); and (iii) the oligonucleic acids of the probe preferably are not extended or otherwise modified by the enzyme, e.g., the polymerization activity of the polymerase.

In another embodiment of the present inventive method, an additional quantity of the second oligonucleic acid (which comprises a quencher) is added to the vessel prior to closing the vessel and incubating the reaction mixture under amplification conditions so as to obtain a molar ratio of the second oligonucleic acid comprising a quencher to the first oligonucleic acid comprising a fluorophore that is greater than 1, optionally not less than 1.1 or 1.2, and is less than 20, preferably not greater than 5, more preferably not greater than 2.5, yet more preferably not greater than 2, and optionally is not greater than 1.5.

In a preferred embodiment of the inventive method, the probe is prevented from interfering with, or participating in, the PCR polymerization step by linking to the 3' terminal end of the nucleic acid an organic or inorganic moiety capable of blocking nucleic acid polymerization known in the art. Advantageously, this polymerization blocking moiety can be a fluorophore or a quencher molecule and can be attached to one or both of the oligonucleic acids of the probe by a linking moiety, or by making the 3'-terminal nucleotide a dideoxynucleotide. Similarly, the oligonucleic acids of the probe can be completely or partially a PNA such that the oligonucleic acid of the probe cannot prime enzyme-mediated polymerization. Alternatively, the 3' end of the oligonucleic acid is rendered impervious to the 5'→3' extension activity of a polymerase by including one or more modified polymerase resistant internucleotide linkages into the 3' end of the oligonucleotide, such as without limitation a phosphonate or phosphothiorate linkage. Similarly, a non-complementary sequence to the nucleic acid of interest can be attached to the 3' end of one or both of the oligonucleic acids of the probe such that the mismatch impedes or prevents enzyme-mediated polymerization.

In another preferred embodiment, oligonucleic acids of the probe of the present invention can be made resistant or impervious to exonuclease digestion. Suitable methods of impeding or preventing exonuclease digestion include (without limitation) introducing a 5' extension that is not complementary to the nucleic acid of interest, adding a non-phosphodiester linkage between two nucleotidyl bases of the oligonucleic acid, and adding an organic or inorganic blocking moiety known in the art (per se) to the 5' end of one or both the oligonucleic acids.

Similarly, enzymatic degradation of the oligonucleic acids of the probe can be impeded or prevented by using an amplification enzyme that lacks such activity. In the case of amplification-based reactions, for example, a polymerase which lacks a 5'→3' exonuclease activity can be used. Polymerases lacking a 5'→3' exonuclease activity are known in the art and include without limitation the Klenow fragment of DNA polymerase I, T4 DNA polymerase, and T7 DNA polymerase, the Stoffel fragment of Taq polymerase, and other like 5'→3' exonuclease minus DNA polymerases.

The polymerase optionally can also be rendered inactive, at least with respect to its exonuclease activity, during the hybridization step. Such inactivation can be achieved in a number of ways including (i) introducing a temperature sensitive inhibitor into the reaction which will inhibit the 5'→3' exonuclease activity of the polymerase at the hybridization temperature, e.g., a solid adsorbent, a specific antibody molecule, or other like reversible or irreversible polymerase inhibitors; (ii) using a polymerase whose activity is greatly reduced at the hybridization temperature; or (iii) introducing an enzyme deactivation step prior to the hybridization step which irreversibly deactivates the polymerase enzyme, i.e., an extended period at high temperature.

In certain embodiments, the reverse transcription efficiency is increased by using a probe comprising an oligonucleic acid that is complementary to a target RNA of interest that has a $T_m$ (melting temperature) of the first oligonucleic acid to the second oligonucleic acid that is lower than the temperature at which the reaction mixture is incubated during reverse transcription. While not desiring to be bound by any particular theory, it is believed that, by carrying out the reverse transcription step at a temperature above each of the Tm of the probe, the probe does not compete with the target RNA by competitively binding to the enzyme mediating reverse transcription.

Similarly, in embodiments employing reverse transcription in the presence of the probe, neither (or none) of the oligonucleic acids of the probe bind to the target RNA at the temperature at which reverse transcription occurs.

EXAMPLES

The present invention will be further clarified by the following examples, which are only intended to illustrate the present invention and are not intended to limit the scope of the present invention.

Example 1. Effect of the Length Difference Between the Two Oligonucleic Acids of a Nucleic Acid Probe on Mismatch Tolerance Evaluated by Melting Curve Assays Melting reactions were performed in a Stratagene Mx4000 multiplex quantitative PCR system with the following cycle conditions: 1 cycle of denaturation at 95° C. for 3 min; 75 cycles of 1-minute holding at a range of temperatures from 85° C. to 10° C. with an 1° C. decrement per cycle. Fluorescein (FAM) fluorescence measurements were recorded during each 1-minute hold of the 75 cycles. At the end of each run, the data were analyzed and melting curves were generated.

Table 2 sets forth the sequences of PCR primers and linear probes used in this and the following examples.

TABLE 2

| Name | Sequence |
|---|---|
| PCR Primers | |
| FP-29 | 5'-ATTCCCTACAATCCCCAAAGTCAAGGAGT-3' (SEQ ID NO: 1) |
| RP-25 | 5'-CCCCTGCACTGTACCCCCCAATCCC-3'(SEQ ID NO: 2) |
| RP-24 | 5'-CCCCTGCACTGTACCCCCCAATCC-3'(SEQ ID NO: 3) |
| Linear Probes[1] labeled with FAM | |
| 520-20 | 6-FAM-(5')-ACAGCAGTACAAATGGCAGT-(3')-DABCYL (SEQ ID NO: 4) |
| 520-31 | 6-FAM-(5')-ACAGCAGTACAAATGGCAGTATTCATCCACA-(3')-DABCYL (SEQ ID NO: 5) |
| lin-41 | 6-FAM-(5')-GCTACAGCAGTACAAATGGCAGTATTCATCCACAATTTCCC-(3')-DABCYL (SEQ ID NO: 6) |
| slin-47 | 6-FAM-(5')-GCACAGCAGTACAAATGGCAGTATTCATCCACAATTTTAAAAGAAAA-(3')-DABCYL (SEQ ID NO: 7) |
| dfam-50 | 6-FAM-(5')-GCACAGCAGTACAAATGGCAGTATTCATCCACAATTTTAAAAGAAAACGC-(3')-6-FAM (SEQ ID NO: 8) |
| fam-650 | 6-FAM-(5')-GCACAGCAGTACAAATGGCAGTATTCATCCACAAT(dT-FAM)TTAAAAGAAAACGC-(3')-6-FAM (SEQ ID NO: 9) |

TABLE 2-continued

| Name | Sequence |
|---|---|
| Quenching Oligos[2] labeled with DABCYL | |
| que-12 | (5')-GTA<u>TTGTACTGCTGT</u>-(3')-DABCYL (SEQ ID NO: 10) |
| que-14 | (5')-CGG<u>ATTTGTACTGCTGT</u>-(3')-DABCYL (SEQ ID NO: 11) |
| que-16 | (5')-GAC<u>CCATTTGTACTGCTGT</u>-(3')-DABCYL (SEQ ID NO: 12) |
| que-22 | DABCYL-(5')-GAC<u>CCATTTGTACTGCTGTAGC</u>-(3')-DABCYL (SEQ ID NO: 13) |
| que-23 | DABCYL-(5')-TGA<u>GCCATTTGTACTGCTGTAGC</u>-(3')-DABCYL (SEQ ID NO: 14) |
| sque-15BH | 5'-<u>TTTGTACTGCTGTGC</u>-(3')-BHQ-1 (SEQ ID NO: 15) |
| bhq-5015 | BHQ-1-(5')-<u>GCGTTTTCTTTTAAA</u>-(3')-BHQ-1 (SEQ ID NO: 16) |

[1]Sequences substantially complementary with targets are underlined ("m").
[2]Sequences substantially complementary with linear FAM probes are underlined ("n").

In each assay, 100 µl reaction contained 1.25×RT-PCR buffer (62.5 mM Bicine, pH 8.05-8.25, 143.75 mM potassium acetate, 10% glycerol, 0.125 mM EDTA, 0.0125 mg/ml acetylated bovine serum albumin (acetylated-BSA), 0.078% (v/v) Tween 20, and 0.025% (w/v) sodium azide), 2.5 mM MnCl$_2$, 0.2 µM FAM-labeled oligonucleic acid ("oligo"), 0.2 µM DABCYL-labeled quenching oligo and 1 µM single-stranded complementary target oligo that was 48 nucleotides long and comprised 0, 1, 2, 3, or 4 mismatches with the FAM labeled oligo (oligos were obtained from Sigma-Genosys). The length of the FAM-labeled oligo was either 20 or 31 nucleotides long, while the DABCYL-labeled quenching oligo was 12, 14 or 16 nucleotides in length. FIGS. 1A-F show the melting curves of a series of double-stranded linear probe sets in the presence or absence of target oligos with different numbers of mismatches, ranging from 0 to 4. The FAM fluorescence intensity was measured as a function of temperature. (A) 520-20/que-16; (B) 520-20/que-14; (C) 520-20/que-12; (D) 520-31/que-14; (E) 520-20/que-12; (F) 520-31/que-14. Positions of mismatches ("mis" hereinafter) for (A)-(C) are as follows: 1 mis is the 12$^{th}$ nucleotide; 2 mis are the 12$^{th}$ and 18$^{th}$ nucleotides. Positions of mismatches for (D) are: 1 mis is the 12$^{th}$ nucleotide; 3 mis are the 12$^{th}$, 18$^{th}$ and 27$^{th}$ nucleotides. Positions of mismatches for (E) are; 1 mis is the 3$^{rd}$, 9$^{th}$ or 12$^{th}$; 2 mis are the 9$^{th}$ and 12$^{th}$ nucleotides. Positions of mismatches for (F) are following: 1 mis is the 12$^{th}$; 2 mis are the 9$^{th}$ and 27$^{th}$, the 21$^{st}$ and 27$^{th}$, the 24$^{th}$ and 27$^{th}$, the 3$^{rd}$ and 27$^{th}$ or the 9$^{th}$ and 12$^{th}$ nucleotides; 3 mis are the 24$^{th}$, 25$^{th}$ and 27$^{th}$ or the 12$^{th}$, 21$^{st}$ and 27$^{th}$ nucleotides; 4 mis are the 21$^{st}$, 24$^{th}$, 25$^{th}$ and 27$^{th}$ nucleotides. All mismatched nucleotide positions start from the 5' end of each respective HIV FAM linear probe.

Figure 1B:
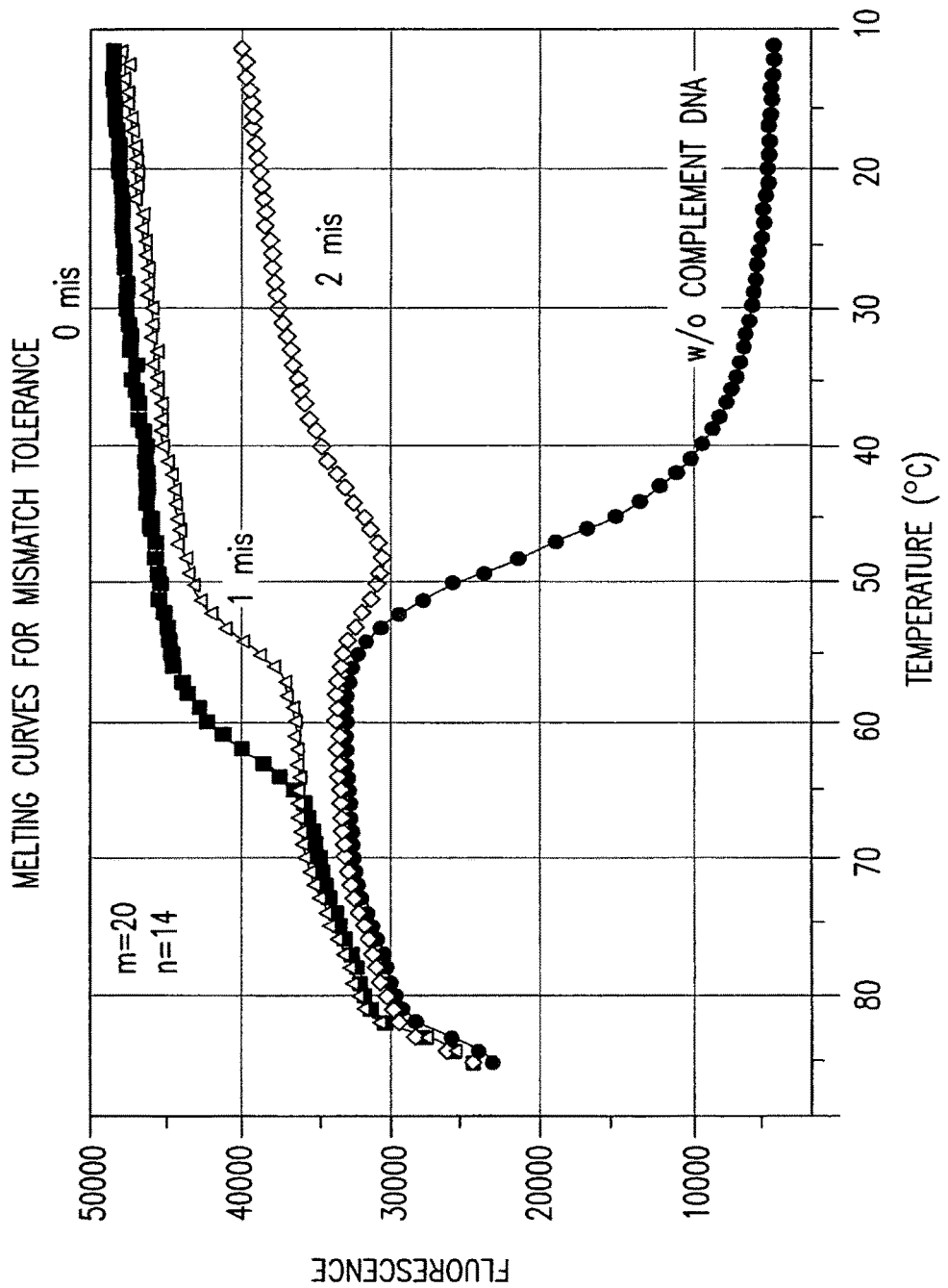
Figure 1C:
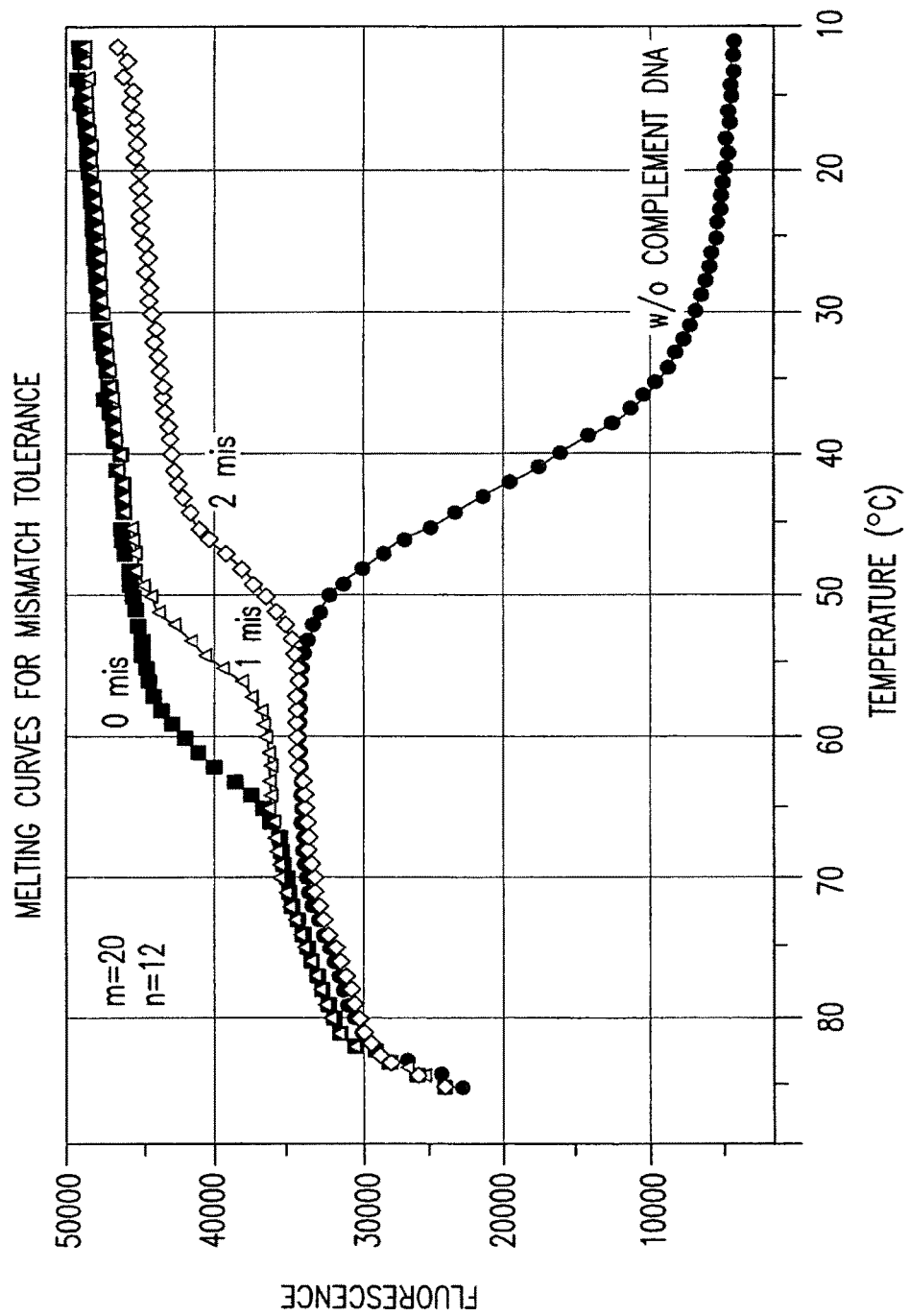
Figure 1D:
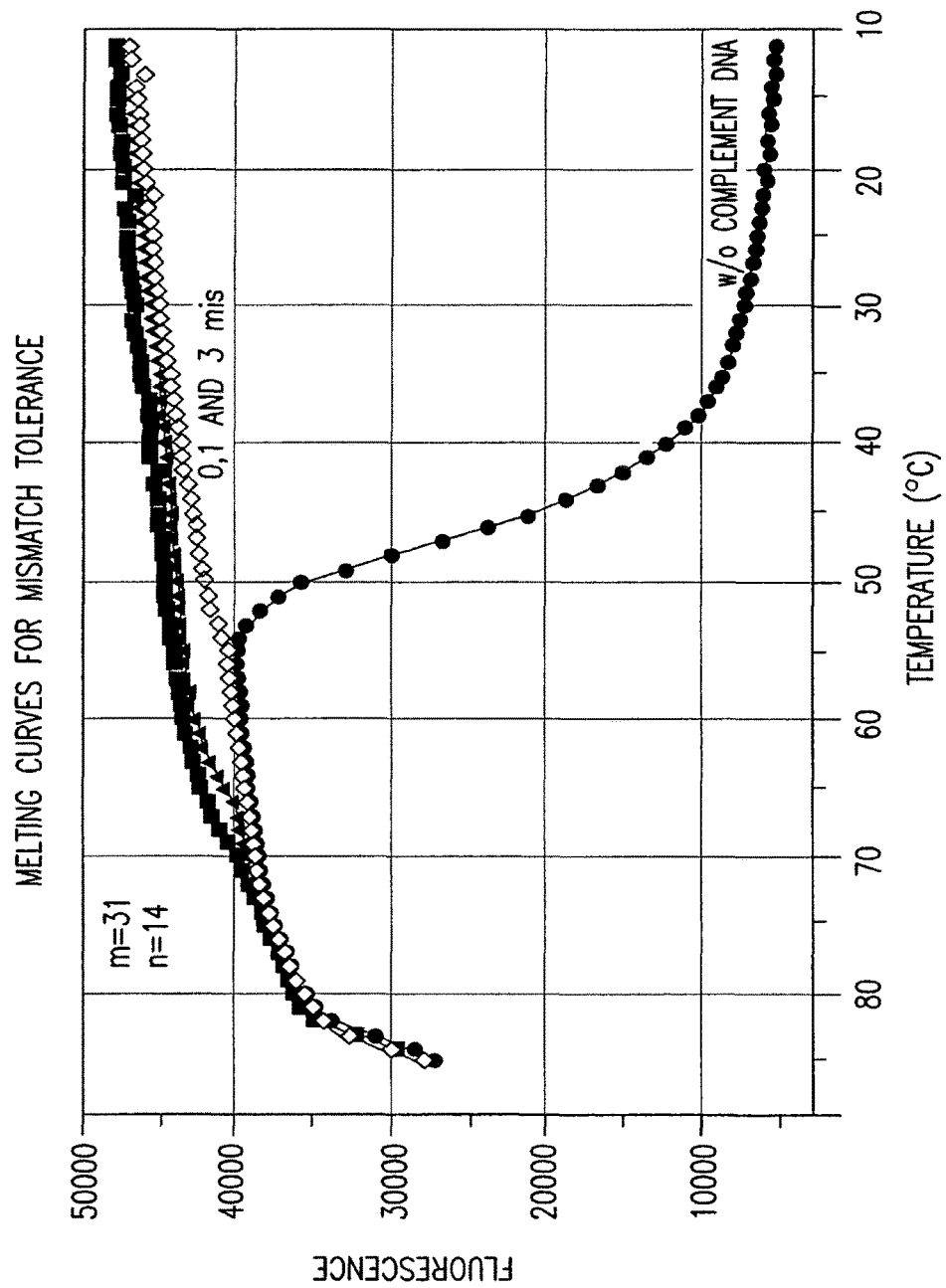
Figure 1E:
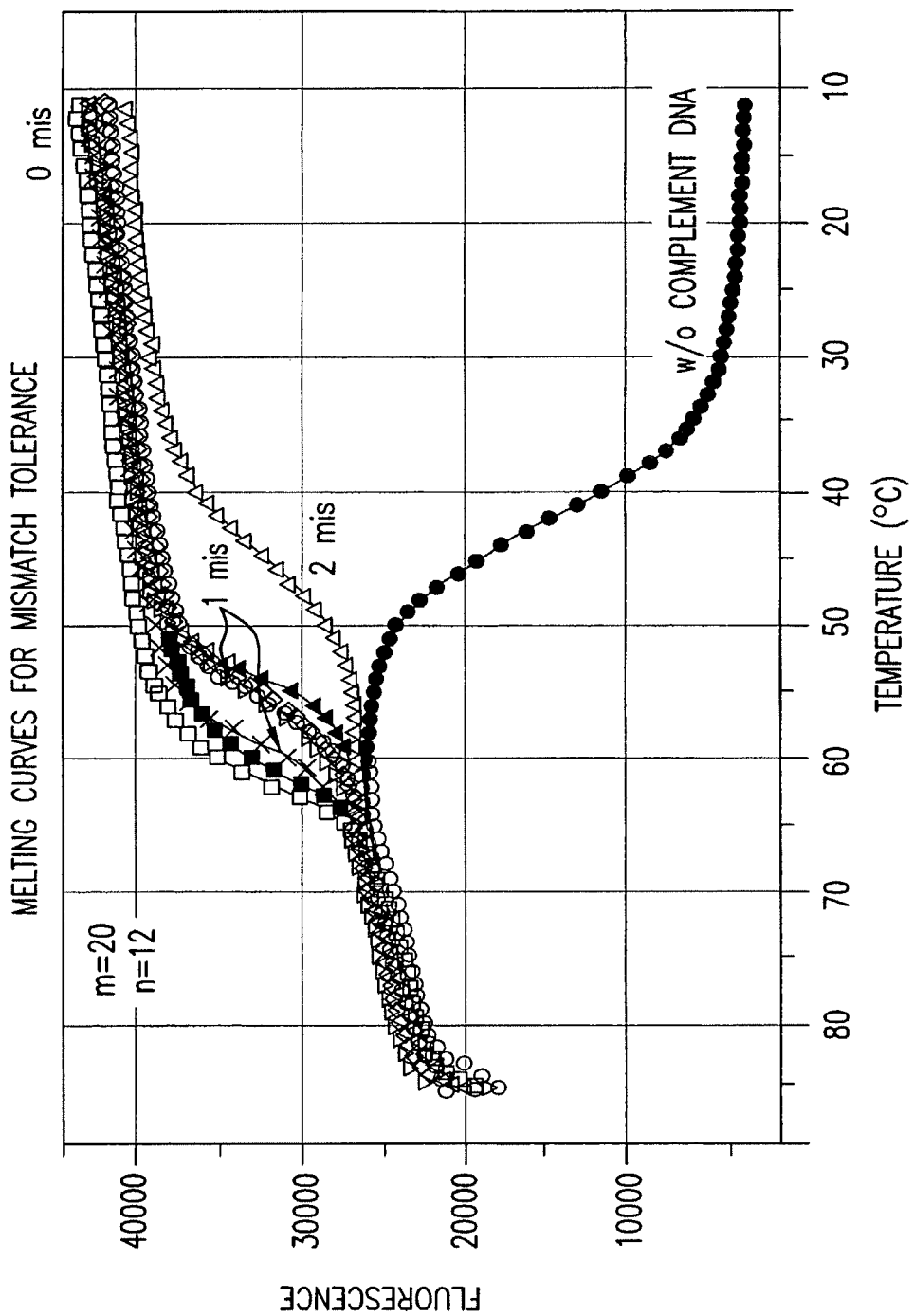
Figure 1F:
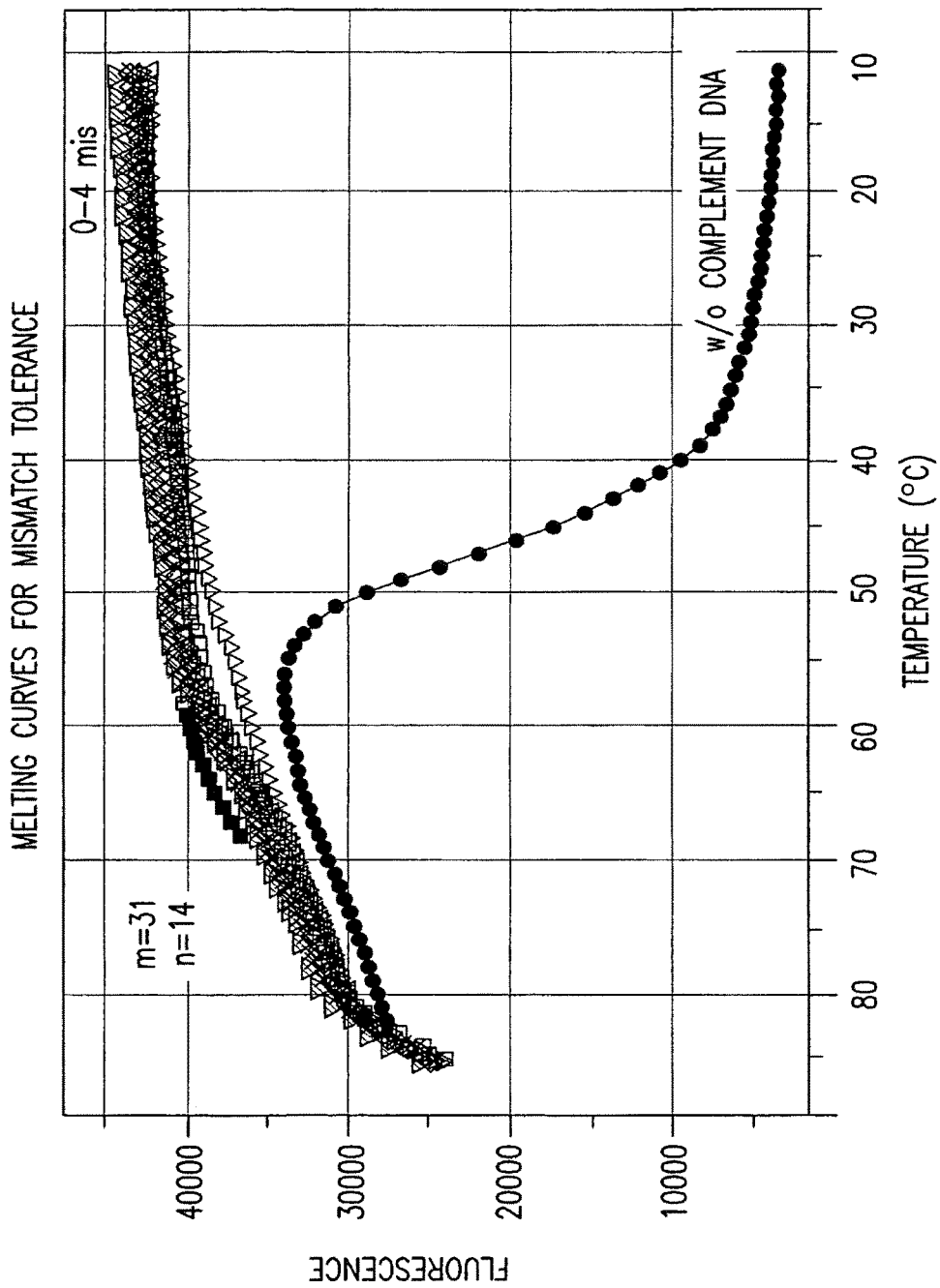

At high temperatures, the FAM-labeled oligo and the shorter complementary DABCYL-labeled quenching oligo of each double-stranded linear probe set were separated, thus leading to the restoration of FAM fluorescence. In the absence of target oligo, these two oligos tended to gradually hybridize with each other as the incubation temperature decreased and formed a non-fluorescent duplex due to the close proximity of the fluorophore FAM and the quencher DABCYL. The Tm's of the quenching oligos determined the incubation temperatures at which the non-fluorescent duplexes started to form. The quenching oligo que-16 carrying a length of 16 complementary nucleotides (Table 2) began the formation of the non-fluorescent duplexes at about 60° C. (FIG. 1A), whereas the 14-base (que-14; Table 2) and 12-base (que-12; Table 2) quenching oligos started it at around 55° C. and 50° C., respectively (FIGS. 1B and C). In the presence of target oligos with 0 mismatches, the quenching oligos, which were shorter and thus had lower Tm than the target oligos, were unable to compete with the target oligos for binding to the FAM-labeled oligos, thus resulting in the formation of probe-target hybrids that fluoresced (FIGS. 1A-F). In the presence of target oligos with mismatches, the 12-base quenching oligo que-12 was still unable to compete with the target oligos with 1 or 2 mismatches for binding to the 20-base FAM-labeled oligo 520-20 (Table 2) (FIG. 1C); the 14-base quenching oligo que-14, on the other hand, was still unable to compete with the target oligo with 1 mismatch but managed to bind to the FAM oligo 520-20 in the presence of the target oligo with 2 mismatches (FIG. 1B). In contrast, the 16-base quenching oligo que-16 was able to bind to 520-20 in the presence of 1 mismatch and even more so in the presence of 2 mismatches (FIG. 1A). These results demonstrate that extending the length of a quenching oligo reduced the capability of its complementary FAM-labeled oligo to bind to target oligos with mismatches. In other words, increasing the length difference between the FAM-labeled oligo and its complementary DABCYL-labeled quenching oligo enhances the level of tolerance of the FAM-labeled oligo to target oligos with mismatches. The same conclusion can be drawn when comparing the melting curves of linear probe set 520-20/que-14 (FIG. 1B) with those of 520-31/que-14 (FIG. 1D). The probe set 520-31/que-14 was even able to pick up the target oligo with 4 mismatches as efficiently as the one with 0 mismatches over a broad range of hybridization. temperatures (FIG. 1F).

Figure 2A:
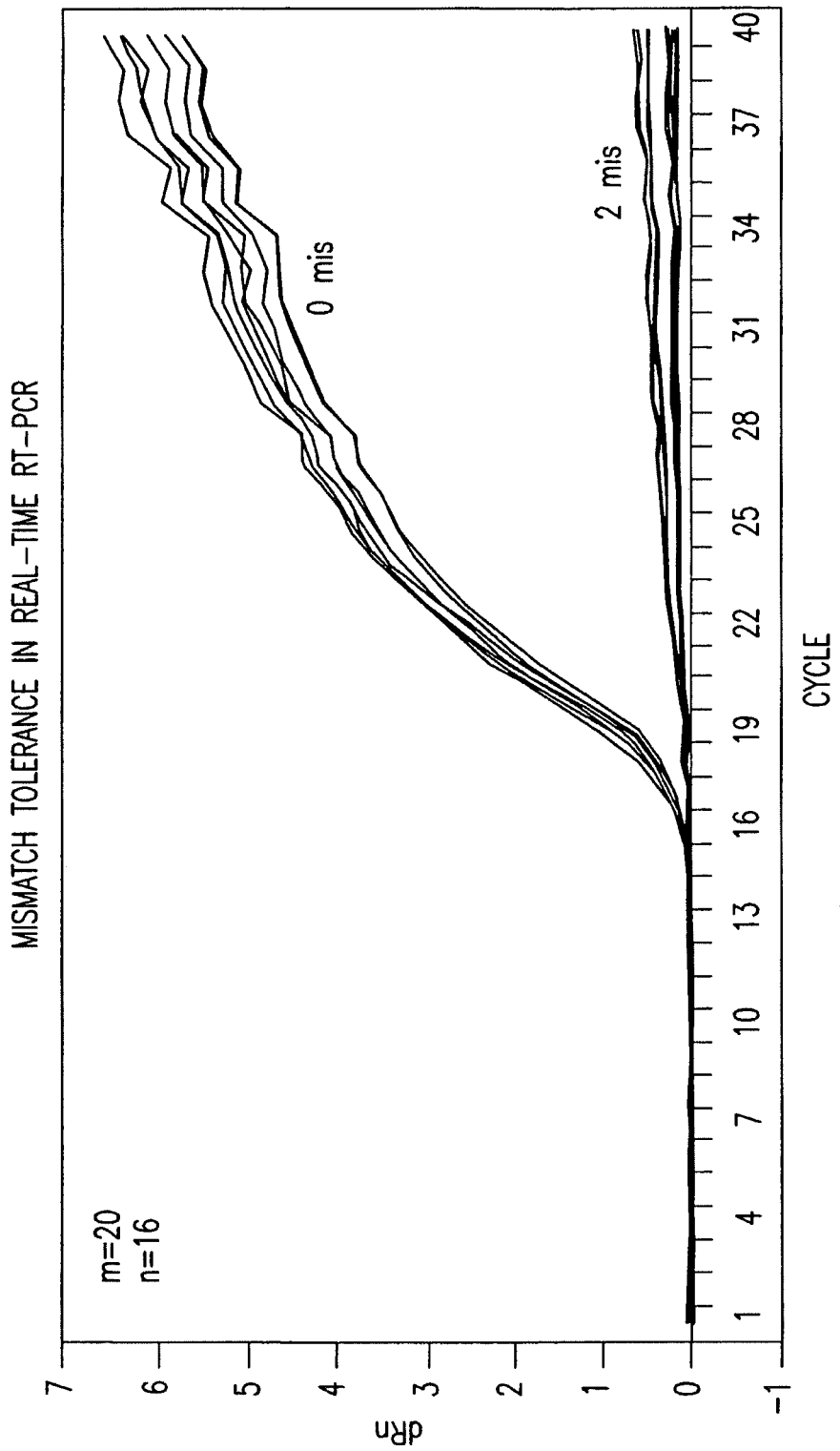
FIG. 2A-C illustrates the comparison of real-time RT-PCR amplification plots of wild type transcript with those of mutated transcripts (as indicated next to each curve).
Figure 2B:
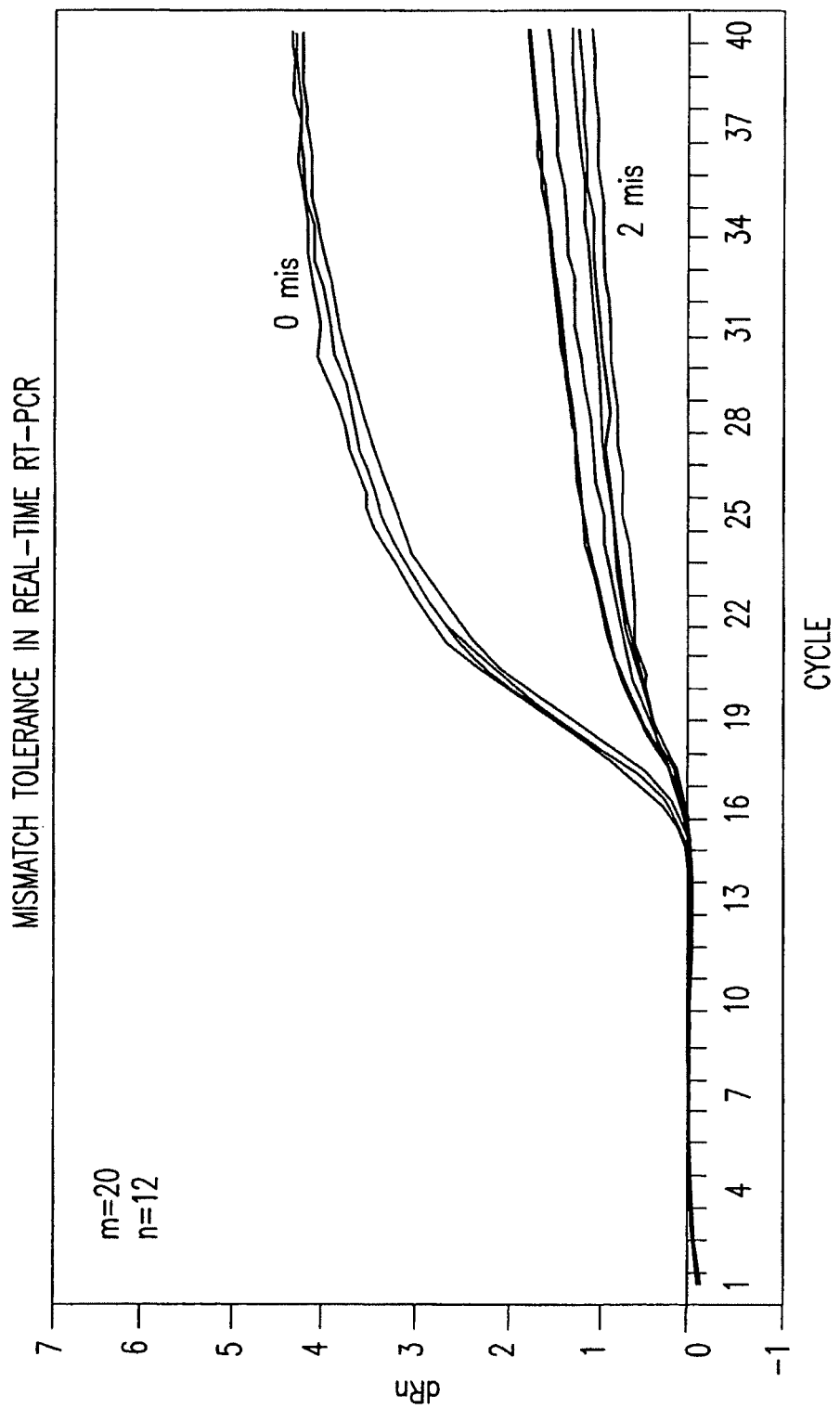
Figure 2C:
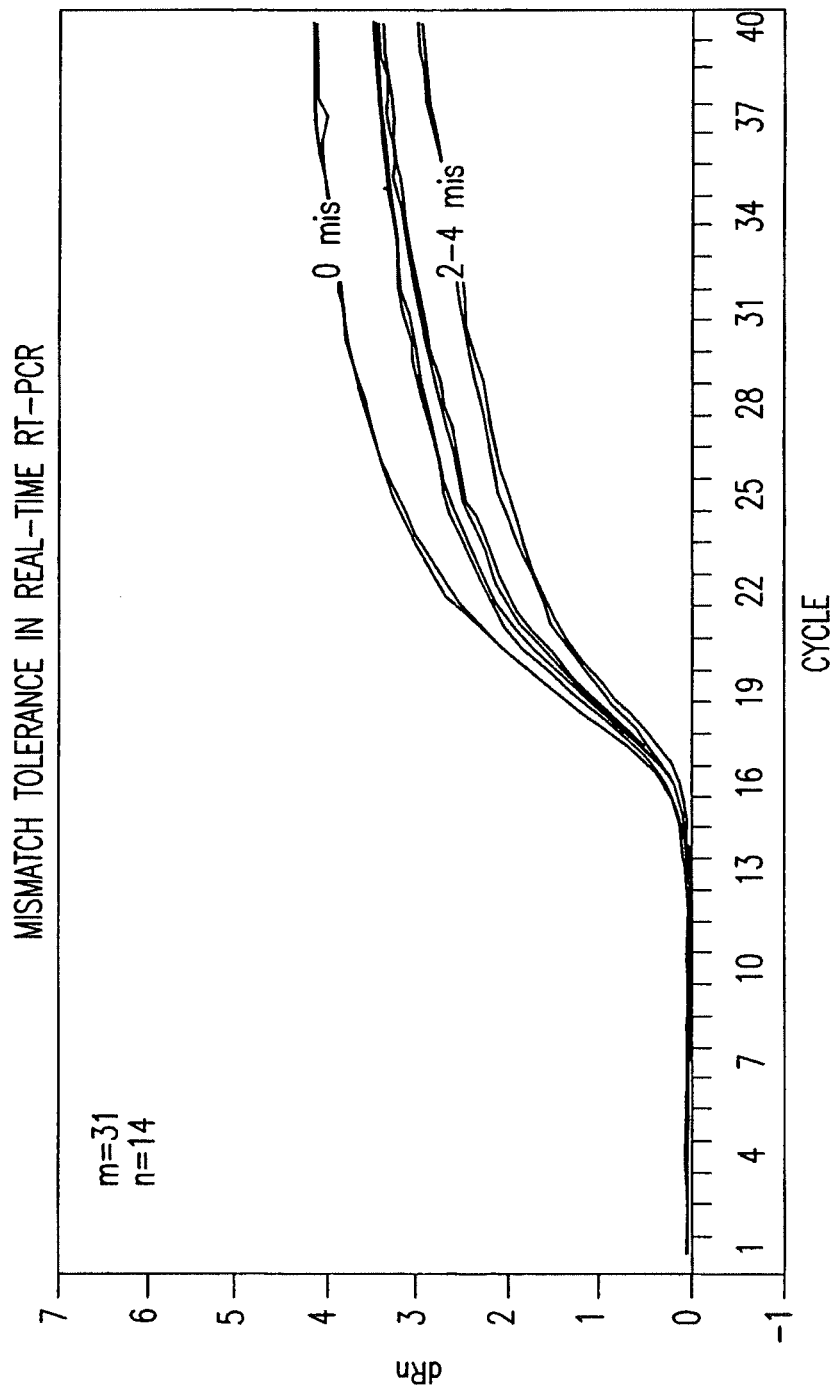

Example 2. Effect of the Length Difference Between the Two Oligonucleic Acids of a Nucleic Acid Probe on Mismatch Tolerance Evaluated by Quantitative Real-Time RT-PCR Assays This example shows the evaluations on three different probe sets 520-20/que-16, 520-20/que-12 and 520-31/que-14 for their mismatch tolerances by performing the quantitative real-time RT (reverse transcription)-PCR assays. Five transcripts carrying different mutations were employed to test these three probe sets. In these non-competitive quantitative assays, each 100 µl RT-PCR reaction contained 1.25×RT-PCR buffer (62.5 mM Bicine, pH 8.05-8.25, 143.75 mM potassium acetate, 10% glycerol, 0.125 mM EDTA, 0.0125 mg/ml acetyl bovine serum albumin (BSA), 0.078% (v/v) Tween 20, and 0.025% (w/v) sodium azide), 2.5 mM MnCl$_2$, 0.375 mM of each deoxynucleotide-triphosphate (dATP, dCTP, dGTP, dTTP), 13.13 units of rTth DNA polymerase (Applied Biosystems), 0.6 µM HIV forward PCR primer FP-29, 1.6 µM HIV reverse PCR primer RP-25 (Table 2), 0.1 µM internal control (IC) forward primer-196, 0.3 µM IC reverse primer-310, 0.2 µM FAM-labeled oligo probe for detection of the HIV PCR products, 0.2 µM DABCYL-labeled quenching oligo for quenching fluorescence signal of the FAM probe, 0.1 µM VIC-labeled beacon probe for detecting the IC PCR products (all fluorophore-labeled and quencher-labeled oligos obtained from TriLink), 1× FRETROX (Applied Biosystems) as the reference dye for signal normalization, 5,000 copies of IC transcript and different levels of HIV wild type transcript standards (0, $4.17\times10^1$, $4.17\times10^2$, $4.17\times10^3$, $4.17\times10^4$ or $4.17\times10^5$ copies per reaction). To quantify the five transcripts by each of the three probe sets, each transcript at $1\times10^4$ copies/reaction was used to run the assay along with the wild type transcript standards. Amplification reactions were performed in an Applied Biosystems 7000 Sequence Detection PCR system with the following cycle conditions: 1 cycle of reverse transcription at 59° C. 30 min; 2 cycles of low-stringent amplification at 95° C. 1 Min and 54° C. 1 min; 10 cycles of high-stringent amplification at 95° C. 15 sec and 59° C. 1 min; and 40 amplification and detection cycles of 95° C. 15 sec and 45° C. 2 min 30 sec. Fluorescence measurements were recorded during each 45° C. step of the 40 cycles. At the end of each real-time PCR run, the data was automatically analyzed by the system and amplification plots were obtained. Quantities of the five sample transcripts were determined by using the calibration curve obtained from plotting the $\log_{10}$ HIV standard copy numbers against their respective fluorescence threshold cycles ($C_T$). FIGS. 2A-C show the amplification plots of the five transcripts by using the three double-stranded linear probe sets 520-20/que-16, 520-20/que-12 and 520-31/que-14, respectively. $1\times10^4$ copies of each transcript were amplified, and the amount of PCR products generated at each cycle was detected by one of the three double-stranded linear probe sets: (A) 520-20/que-16; (B) 520-20/que-12; (C) 520-31/que-14. To the five transcripts, the FAM-labeled oligo 520-20 encountered 0 mismatches to two of them and 2 mismatches to the remaining three (Table 4). When paired with the DABCYL-labeled quenching oligo que-16, the probe 520-20 barely detected the three transcripts with 2 mismatches (FIG. 2A) and thus under-estimated their concentrations by more than 1 log 10 (Table 3). On the other hand, when paired with a 4-base shorter quenching oligo que-12, the probe S20-20 was able to detect the three 2-mismatch transcripts at a higher efficiency (FIG. 2B) and only under-estimated their quantities by less than 0.5 log 10 (Table 4). These results confirmed the conclusion from Example 1 that widening the length difference between the two component oligos (the FAM-labeled oligo and its complementary DABCYL-labeling quenching oligo) of a double-stranded linear probe increases the efficiency of the FAM-labeled oligo to pick up target oligos with mismatches. This conclusion was further substantiated by the ability of the probe set 520-31/que-14, with a larger length difference of 17 bases between the two component oligos, to detect transcripts with mutations up to 4 almost as efficiently as the wild type transcript (FIG. 2C). The probe 520-31, which was 11 bases longer than 520-20 and had to identify more mismatches for the same set of the five transcripts (Table 5), quantified all five transcripts to be between $1.3\times10^4$ and $3.1\times10^4$ (Table 5); these determined copy numbers were very close to the expected $1\times10^4$. In the $\log_{10}$ scale, the highest determined copy number difference between the mutant and the wild type was 0.4 $\log_{10}$ that fell within the acceptable 0.5 $\log_{10}$ (Table 5). In conclusion, partially double-stranded probes can be utilized to accurately quantify nucleic acid samples, and when designed appropriately, those probes are able to quantify mutants as accurately as wild types.

TABLE 3

Quantifications of transcripts (4.0 log10 per reaction) with 0 or 2 mismatches by using the double-stranded probe 520-20/que-16

| Number of Mismatches | Positions of Mismatches[1] | Quantity (log 10 cps/reaction) |
|---|---|---|
| 0 | n/a | 4.42 |
| 0 | n/a | 4.41 |
| 2 | 6, 12 | 3.03 |
| 2 | 9, 12 | 2.90 |
| 2 | 12, 18 | 3.37 |

[1]Positions of mismatches show the positions of mismatched nucleotides starting from the 5' end of the HIV FAM probe 520-20.
n/a: not applicable.

TABLE 4

Quantifications of transcripts (4.0 log10 per reaction) with 0 or 2 mismatches by using the double-stranded probe 520-20/que-12

| Number of Mismatches | Positions of Mismatches[1] | Quantity (log 10 cps/reaction) |
|---|---|---|
| 0 | n/a | 4.47 |
| 0 | n/a | 4.46 |
| 2 | 6, 12 | 4.03 |
| 2 | 9, 12 | 4.13 |
| 2 | 12, 18 | 4.13 |

[1]Positions of mismatches show the positions of mismatched nucleotides starting from the 5' end of the HIV FAM probe 520-20.
n/a: not applicable.

TABLE 5

Quantifications of transcripts (4.0 log10 per reaction) with 0, 2, 3 or 4 mismatches by using the double-stranded probe 520-31/que-14

| Number of Mismatches | Positions of Mismatches[1] | Quantity (log 10 cps/reaction) |
|---|---|---|
| 0 | n/a | 4.50 |
| 2 | 6, 12 | 4.31 |
| 3 | 9, 12, 22 | 4.31 |
| 3 | 12, 18, 27 | 4.11 |
| 4 | 21, 24, 25, 27 | 4.31 |

[1]Positions of mismatches show the positions of mismatched nucleotides starting from the 5' end of the HIV FAM probe 520-31.
n/a: not applicable.

Figure 3A:
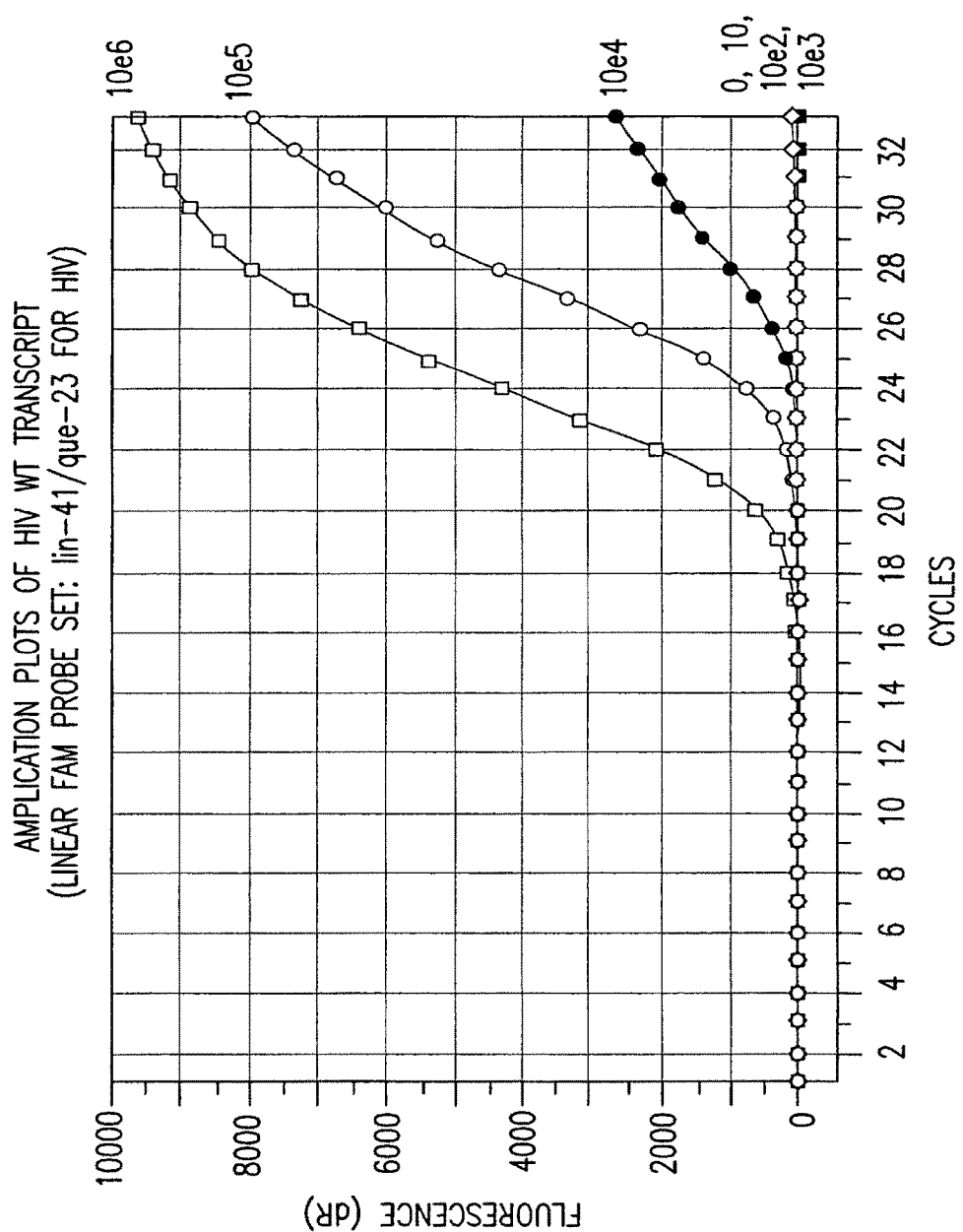
FIG. 3A-B graphically presents real-time measurement of amplicon synthesis during RT-PCR reactions using the partially double-stranded linear probe set lin-41/que-23 using (A) HIV wild type template transcripts and (B) internal control transcript at 100 copies per reaction mixture.
Figure 3B:
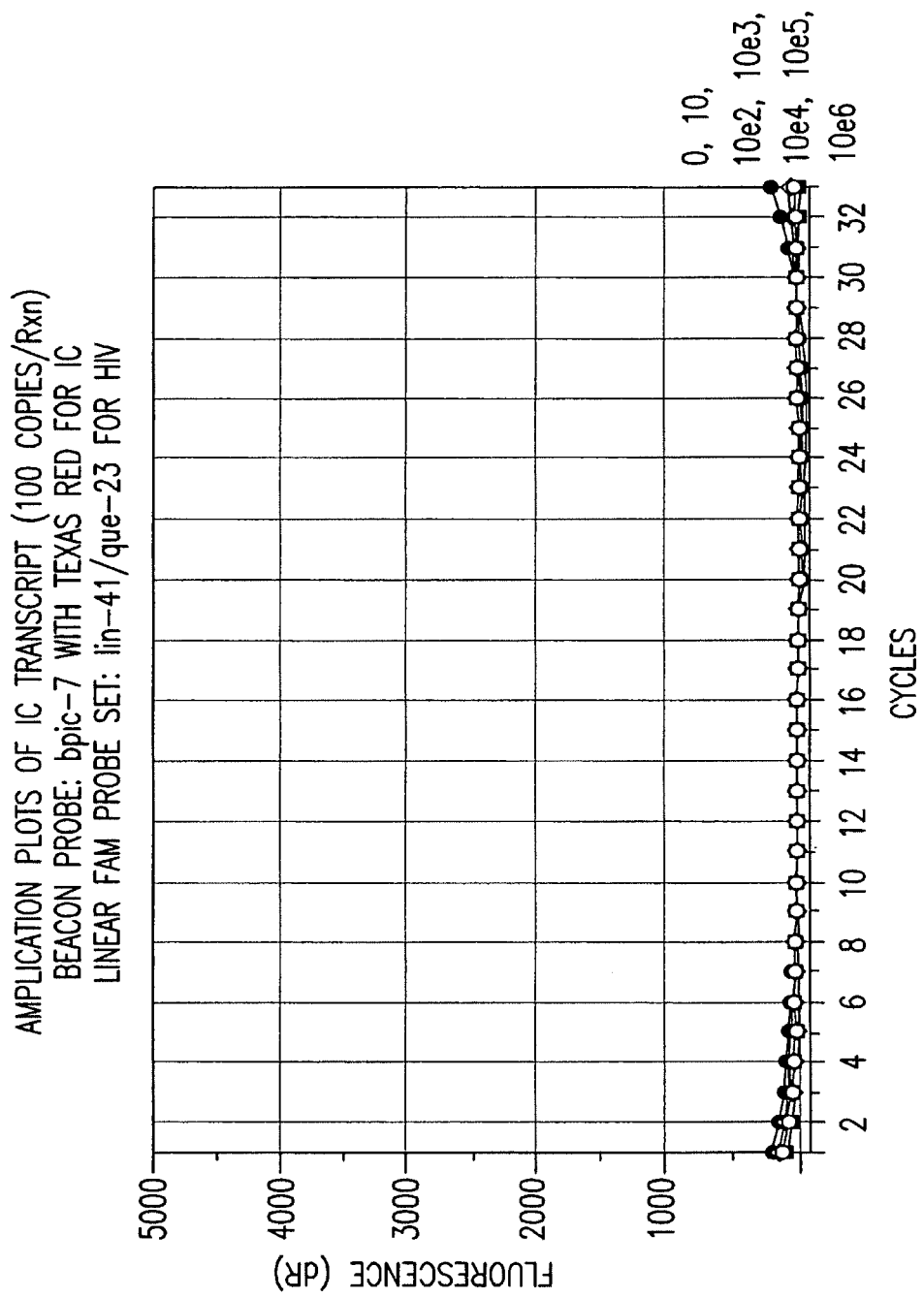

Example 3. Inhibition of RT-PCR by a Quenching Oligonucleotide with a Tm Higher than the RT Temperature To examine the impact of utilizing a quencher probe with a Tm that is above the incubation temperature of the RT reaction, performance of the probe combination, lin-41 and que-23 (Table 2), was evaluated in a quantitative real-time reverse transcription (RT)-PCR assay. The quenching oligo, que-23, has a Tm of 60.27, above the 59° C. RT incubation temperature. In this competitive quantitative assay, each 100 µl RT-PCR reaction was carried out in the presence of 1×EZ buffer (containing 50 mM Bicine, pH 8.2, 115 mM potassium acetate and 8% glycerol), 2.5 mM Mn(OAc)2, 0.4 mM of each deoxynucleotide-triphosphate (dATP, dCTP, dGTP, dTTP), 20 units of RNase inhibitor, 10 units of Tth DNA polymerase (all from Applied Biosystems), 0.2 µM HIV forward PCR primer FP-29, 1.0 µM HIV reverse PCR primer RP-24, 0.1 µM FAM-labeled oligo probe lin-41 for detection of the HIV wild type PCR products, 0.2 µM DABCYL-labeled quenching oligo que-23 to quench the FAM probe, 0.1 µM Texas Red-labeled beacon probe bpic-7 for detecting the internal control (IC) PCR products, 0.04 µg/ml Alexa (Molecular Probes) as the reference dye for signal normalization, 100 copies of internal control transcript and different copy numbers of HIV wild type transcript (0, 10, $10^2$, $10^3$, $10^4$, $10^5$ or $10^6$ copies). Amplification reactions were performed in a Stratagene Mx4000 multiplex quantitative PCR system with the following cycle conditions: 1 cycle of reverse transcription at 95° C. 5 sec and 59° C. 30 min; 2 cycles of low-stringent amplification at 95° C. 30 sec, 54° C. 30 sec and 72° C. 30 sec; 10 cycles of high-stringent amplification at 95° C. 30 sec, 59° C. 30 sec and 72° C. 30 sec; 33 amplification and detection cycles of 95° C. 30 sec, 50° C. 1 min and 72° C. 30 sec. Fluorescence measurements were recorded during each 50° C. step of the 33 cycles. At the end of each real-time PCR run, the data was automatically analyzed by the system and amplification plots were obtained. Amplification curves of the wild type and the internal control transcripts are shown in FIGS. 3A and B, respectively. Seven reactions, each initiated with a different number of HIV wild type template transcripts were incubated simultaneously in a Stratagene's Mx4000. The concentration of amplicons that were present after each cycle of amplification was determined by measuring FAM fluorescence signal emanated from the probe-target hybrids during the last 21 seconds of the annealing step. The FAM fluorescence intensity in each reaction was measured as a function of cycle. Of the wild type transcript input levels ranging from $10^1$-$10^6$, significant amplification was observed only for the high copy numbers (i.e. from $10^4$ to $10^6$), whereas no fluorescence signals were recorded for the low copy numbers from 0 to $10^3$. For real-time RT-PCR amplification of control transcripts, 100 copies of internal control transcripts were used. The amount of internal control PCR products generated at each cycle was detected by molecular beacon probe bpic-7 labeled with Texas Red. The copy number of wild type transcript as indicated next to each curve was amplified in an RT-PCR reaction together with the 100 copies of internal control transcript. No fluorescence signals were observed for the 100 copies of internal control transcript. These data are consistent with a hypothesis that the DABCYL-labeled quenching oligo que-23 with a Tm of 60.27, higher than the 59° C. RT temperature, hybridized to the FAM-labeled linear probe lin-41 and that the lin-41/que-23 duplex inhibited reverse transcription. The inhibition significantly reduced reverse transcription efficiency of both wild type and internal control transcripts. No fluorescence signals above baseline were observed at low copy numbers (0-$10^3$), while amplification curves for the high copy numbers ($10^4$-$10^6$) had significantly delayed cycle numbers and reached sub-maximal levels.

Figure 4A:
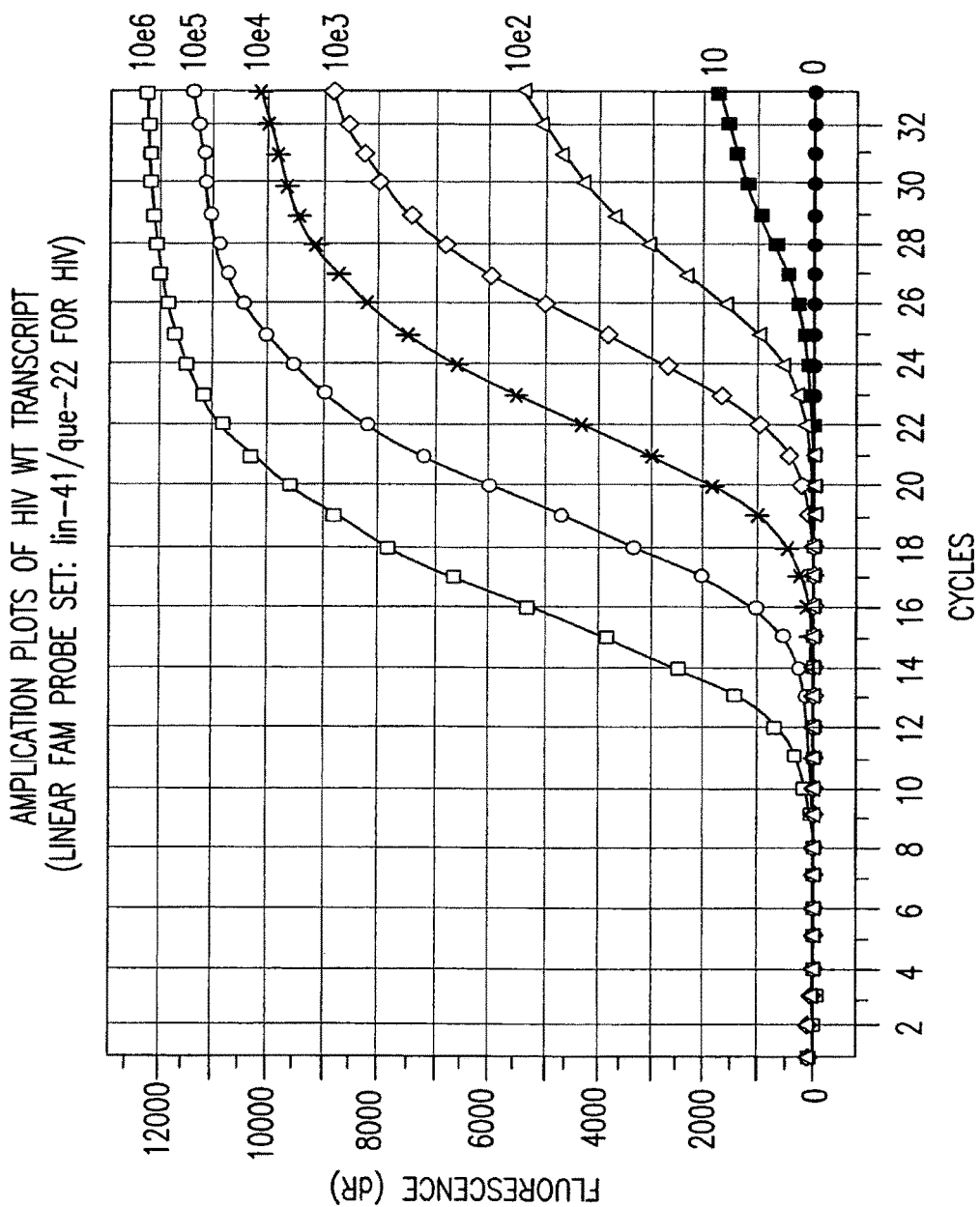
FIG. 4A-B depicts real-time measurements of amplicon synthesis during RT-PCR reactions using the probe set lin-41/que-22 with (A) HIV wild type template transcripts and (B) internal control transcript at 100 copies per reaction mixture.
Figure 4B:
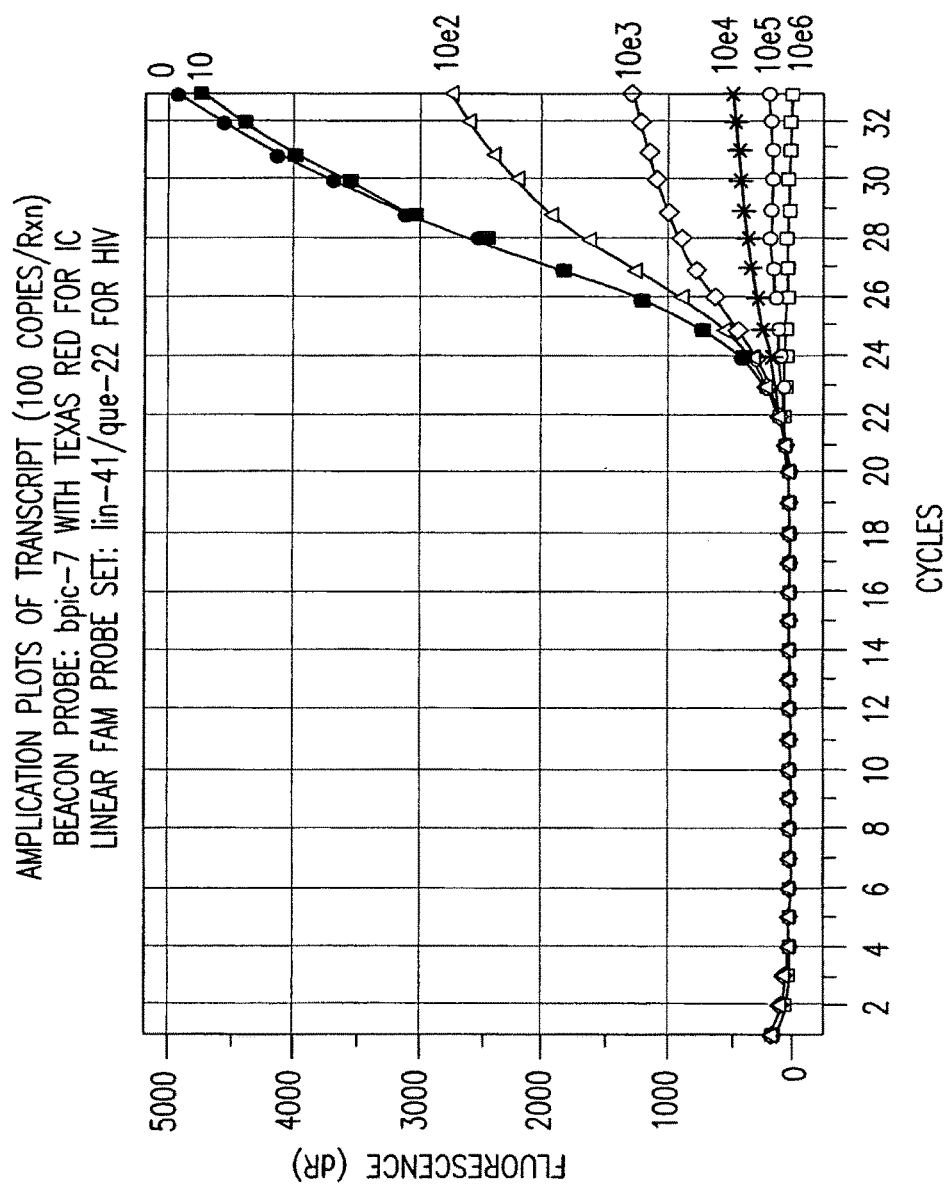

Example 4. Elimination of Inhibition by a Quenching Oligonucleic Acid with a Tm Lower than the RT Temperature in RT-PCR To evaluate the relationship between the Tm of the quenching oligo and RT-PCR assay performance, the FAM-labeled probe, lin-41, was used in combination with the quenching oligo, que-22 (Table 2). The oligo, que-22, has a Tm of 55.86° C., below the 59° C. incubation temperature of reverse transcription (RT). A quantitative real-time RT-PCR assay was performed as described in Example 3, with the exception that the quenching oligo, que-22, was substituted for que-23. The resulting data is presented in FIGS. 4A and 4B. In contrast to results obtained in Example 3, typical amplification curves were found for both wild type and internal control transcripts at all copy levels. The wild type amplification curves at template concentrations of $10^4$, $10^5$ and $10^6$ emerged about 8 cycles earlier and reached to a maximum level higher than 10,000. Even at 10 copies per reaction, the lowest template input level examined, significant amplification was observed 2,000 units). The observed amplification was significantly above the baseline, demonstrating that the probe combination, lin-41/que-22, provides high sensitivity. Moreover, the assay exhibited good linearity with a broad dynamic range; correlation coefficient ($r^2$) of 0.998 over six logs (10 to $10^6$) of target concentration. For the 100 copies of internal control transcript, the amplification curves displayed a typical profile of competitive PCR, in which the internal control fluorescence signals decreased in response to the increase of wild type transcript copy numbers. These data demonstrate the utility of a quenching probe that has a Tm (for the FAM-labeled linear probe) below the RT incubation step for RT-PCR amplification and quantification.

Figure 5B:
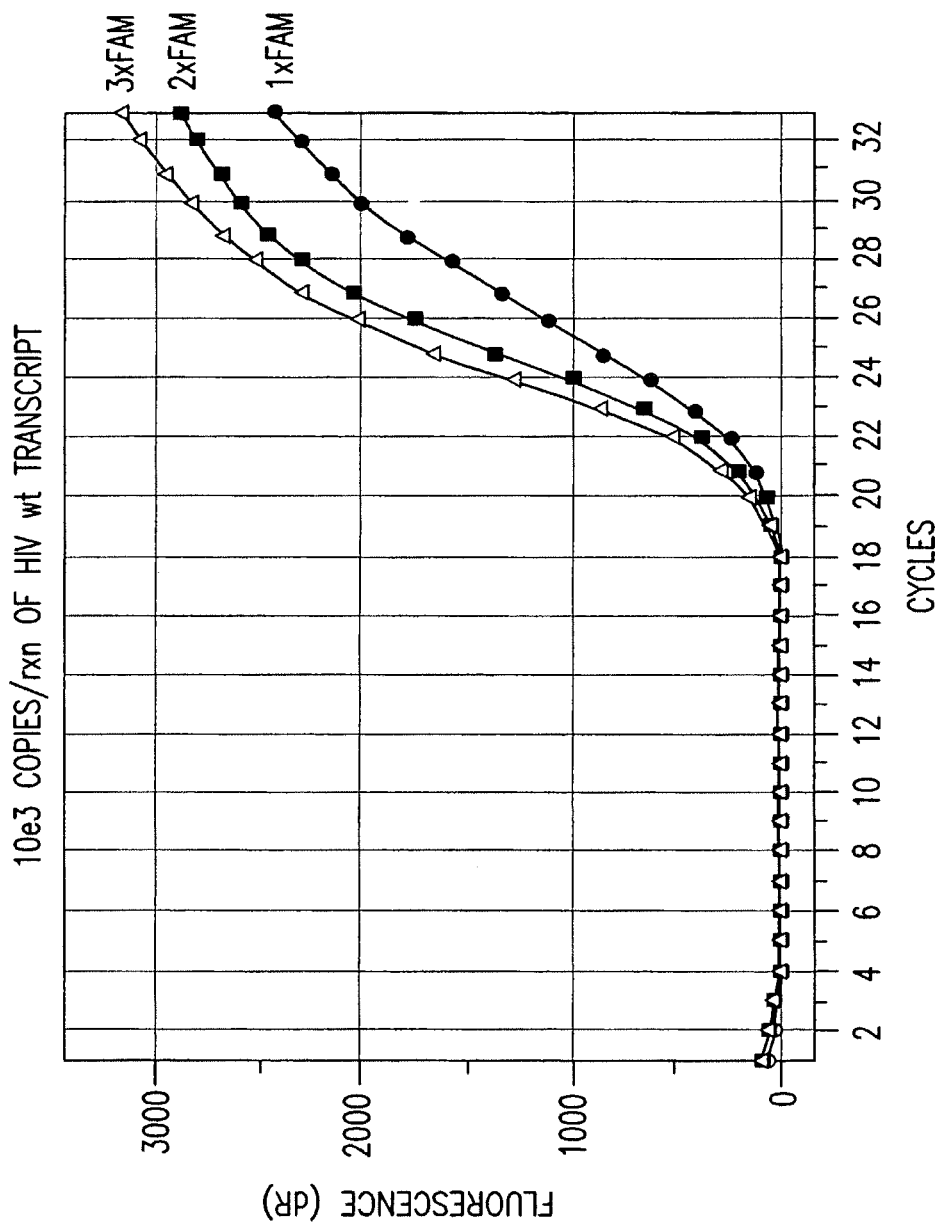
Figure 5C:
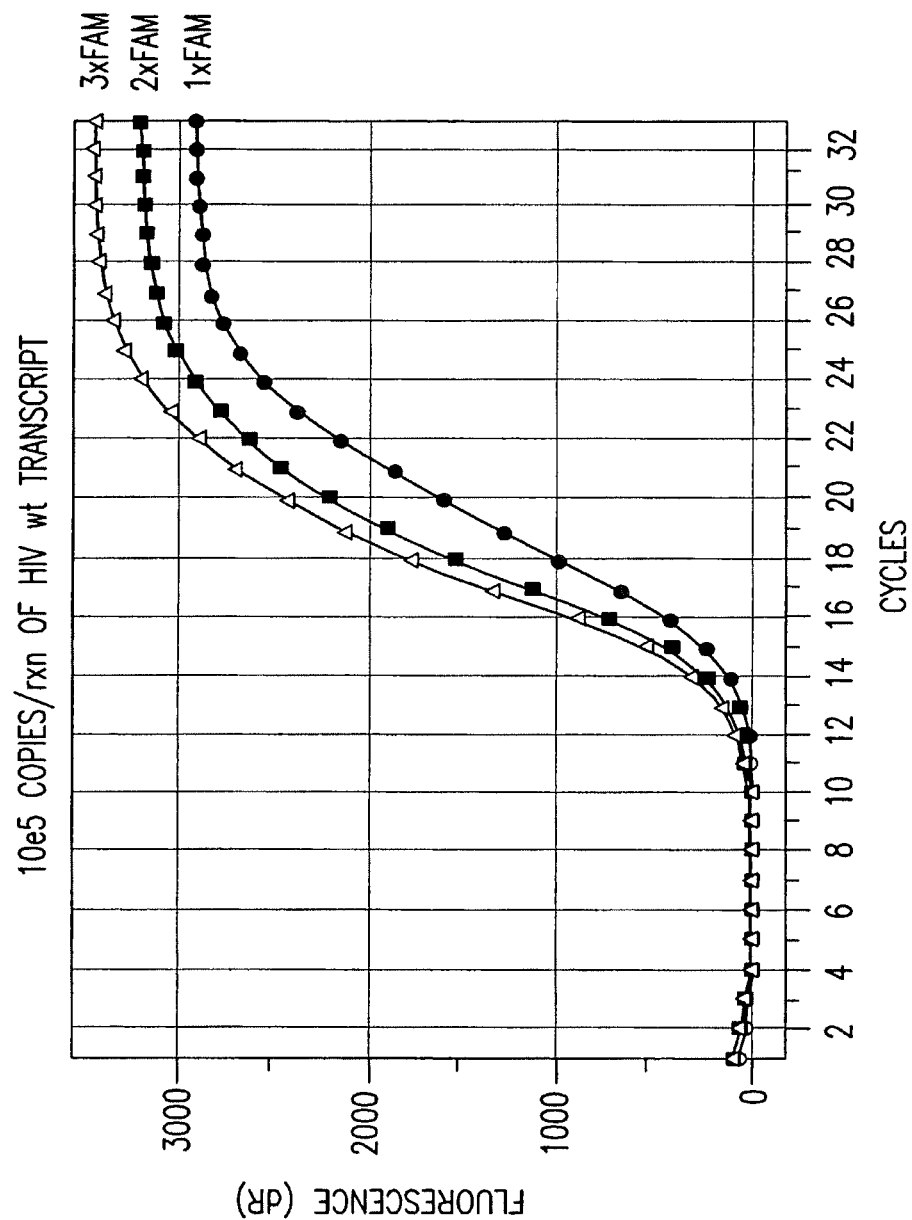
Figure 5D:
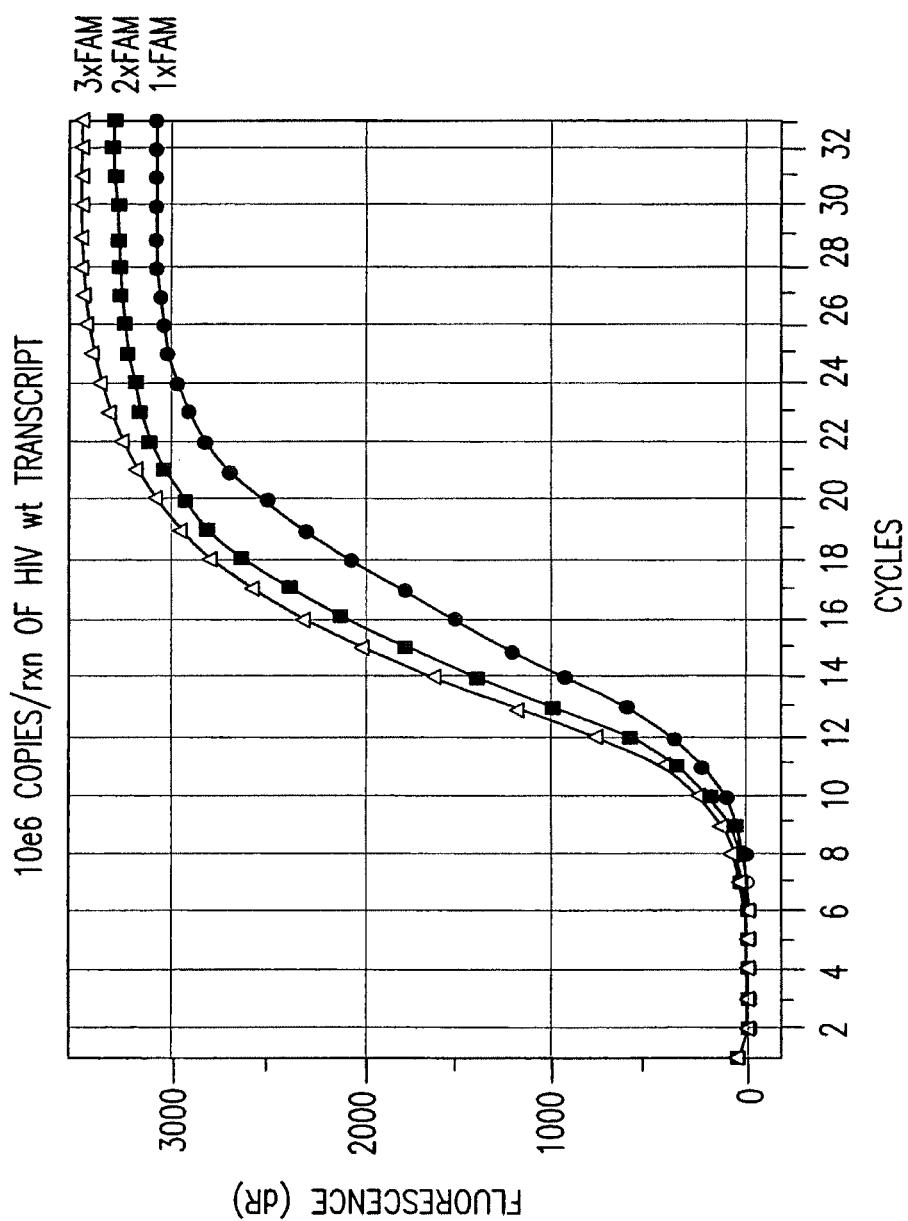

Example 5. Signal Enhancements by Using Linear Probes Labeled with More than One Fluorescent Molecule To examine whether fluorescence signals generated in RT-PCR assays could be enhanced by use of linear probes carrying more than one fluorescent label, a quantitative real-time RT-PCR. assay was set-up with multiply labeled probes. Three FAM-labeled linear probes, slin-47, dfam-50 and fam-650 (Table 2) were used, along with two quenching oligos, sque-15BH and bhq-5015. Both quenching oligo probes bind to all three FAM-labeled linear probes. Probe slin-47 carries one FAM (1×FAM) at the 5' end and a DABCYL at the 3' end, while probe dfam-50 has one FAM at both 5' and 3' ends (2×FAM); probe fam-650 possesses an internal FAM in addition to its two terminal FAMs (3×FAM). The RT-PCR reactions in this competitive quantitative assay were carried out under the condition similar to that described in Example 3. Each 100 µl RT-PCR reaction contained 1×EZ buffer (containing 50 mM Bicine, pH 8.2, 115 mM potassium acetate and 8% glycerol), 2.5 mM Mn(OAc)2, 0.4 mM of each deoxynucleotide-triphosphate (dATP, dCTP, dGTP, dTTP), 20 units of RNase inhibitor, 10 units of Tth DNA polymerase,(all from Applied Biosystems), 0.1 µM HIV forward PCR primer FP-29, 1.0 µM HIV reverse PCR primer RP-24, 0.2 µM FAM-labeled oligo probe (slin-47, dfam-50 or fam-650) for detection of the HIV wild type PCR products, 0.25 µM BHQ-labeled quenching oligo sque-15BH to quench the 5' end of the FAM probe, 0.25 µM BHQ-labeled quenching oligo bhq-5015 to quench the 3' end of the FAM probe, 0.2 µM Texas Red-labeled beacon probe bpic-7BH for detecting the internal control (IC) PCR products, 0.04 µg/ml Alexa as the reference dye for signal normalization, 100 copies of internal control transcript and different copy numbers of HIV wild type transcript (0, 10, $10^2$, $10^3$, $10^4$, $10^5$ or $10^6$ copies). Amplification reactions were performed in a Stratagene Mx4000 multiplex quantitative PCR. system with the following cycle conditions: 1 cycle of reverse transcription at 59° C. 60 min; 2 cycles of low-stringent amplification at 95° C. 1 min and 54° C. 1 min; 10 cycles of high-stringent amplification at 95° C. 15 sec and 59° C. 1 min; 33 amplification and detection cycles of 95° C. 15 sec and 40° C. 2 min 30 sec. Fluorescence measurements were recorded during each 40° C. step of the 33 cycles. At the end of each real-time PCR run, the data were automatically analyzed by the system and amplification plots were obtained. Typical amplification profiles were observed at all input levels of wild type transcript by all three FAM-labeled probes. FIG. 5 depicts amplification plots for wild type transcript at 10 copies/reaction (A), $10^3$ copies/reaction (B), $10^5$ copies/reaction (C) and $10^6$ copies/reaction (D). At each copy number tested, the 3×FAM probe overall generated more fluorescence signal than the 2×FAM probe, which in turn overall emanated more signal than the 1×FAM probe. In addition to an overall higher fluorescence signal level, increasing assay sensitivity, linear probes with multiple FAM labels generated amplification curves with steeper slopes, facilitating determination of the fluorescence threshold cycle ($C_T$).

Example 6. Quantification of Transcripts with or Without Mutations

Figure 6:
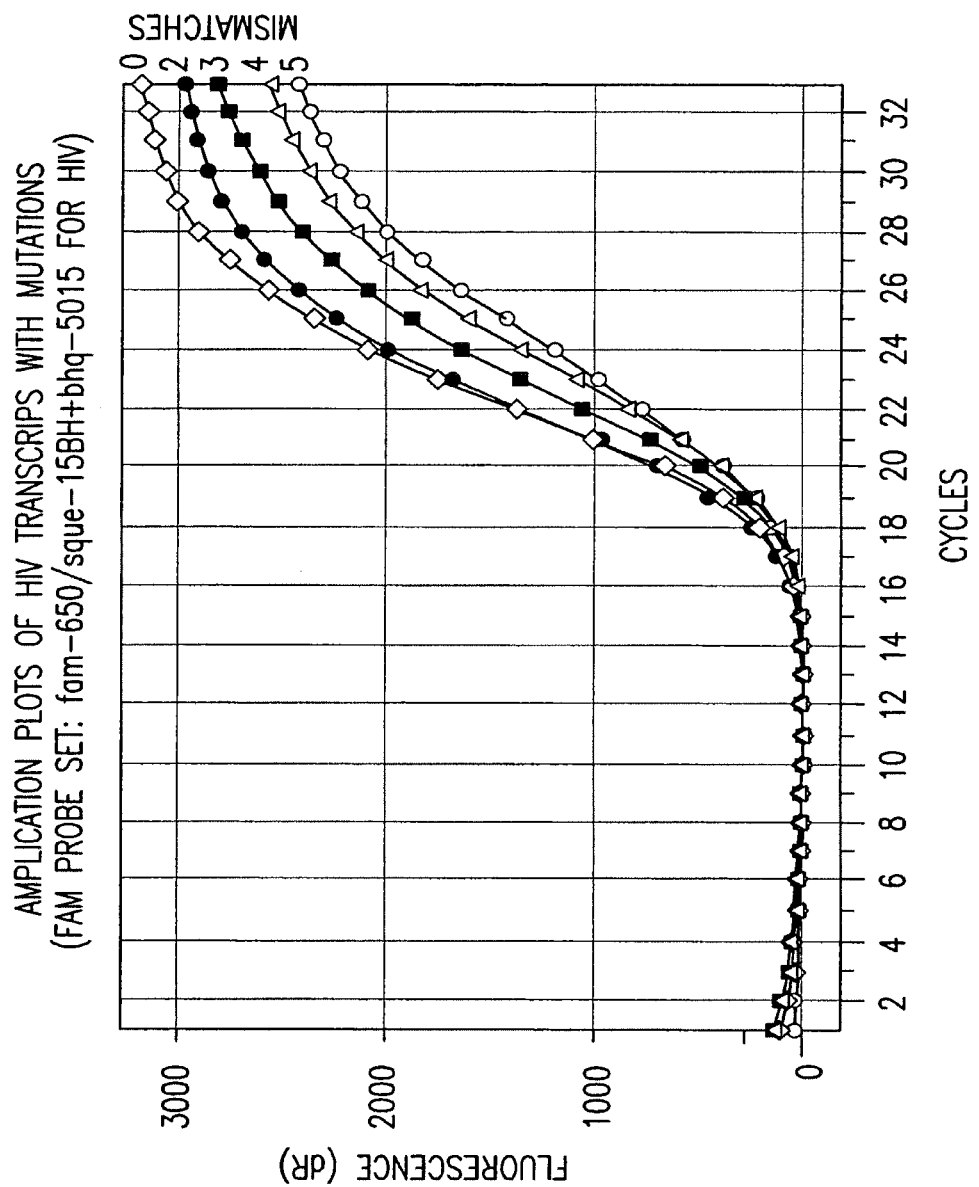
FIG. 6 graphically presents real-time RT-PCR amplification plot data of transcripts with 0, 2, 3, 4 or 5 mutations (as indicated next to each curve).

To examine the utility of partially double-stranded probes for reliably detecting and quantifying templates with mismatches, probe set fam-650 (3 FAM labels)/sque-15BH+bhq-5015 (Table 2) was used to quantify transcripts with multiple mutations. Each of five transcripts carrying 0, 2, 3, 4 or 5 mutations was quantified in a real-time RT-PCR assay. Transcript copy number was determined by OD260 measurement. The assay was standardized using different copy numbers of wild type transcript. The RT-PCR reactions in this competitive quantitative assay were carried out under the condition similar to that described in Example 5. Each 100 μl RT-PCR reaction contained 1×EZ buffer (containing 50 mM Bicine, pH 8.2, 115 mM potassium acetate and 8% glycerol), 2.5 mM Mn(OAc)2, 0.4 mM of each deoxynucleotide-triphosphate (dATP, dCTP, dGTP, dTTP), 20 units of RNase inhibitor, 10 units of Tth DNA polymerase, 0.1 μM HIV forward PCR primer FP-29, 1.0 μM HIV reverse PCR primer RP-24, 0.15 μM FAM-labeled oligo probe fam-650 for detection of the HIV wild type PCR products, 0.25 μM BHQ-labeled quenching oligo sque-15BH to quench the 5' end of the FAM probe, 0.25 μM BHQ-labeled quenching oligo bhq-5015 to quench the 3' end of the FAM probe, 0.1 μM Texas Red-labeled linear probe trp-34 for detecting the internal control (IC) PCR products, 0.1 μM BHQ-labeled quenching oligo etrp-15bhq to quench the Texas Red IC, 0.04 μg/ml Alexa as the reference dye for signal normalization, 200 copies of internal control transcript and different copy numbers of HIV wild type standard transcript (0, 10, $10^2$, $10^3$, $10^4$, $10^5$ or $10^6$ copies). To quantify the five transcripts, $8 \times 10^3$ copies of each transcript instead of the wild type standard were added into one RT-PCR reaction and amplified along with the seven HIV standards. Amplification reactions were performed in a Stratagene Mx4000 multiplex quantitative PCR system with the following cycle conditions; 1 cycle of reverse transcription at 59° C. 60 min; 2 cycles of low-stringent amplification at 95° C. 1 min and 54° C. 1 min; 10 cycles of high-stringent amplification at 95° C. 15 sec and 59° C. 1 min; 33 amplification and detection cycles of 95° C. 15 sec and 40° C. 2 min 30 sec. Fluorescence measurements were recorded during each 40° C. step of the 33 cycles. At the end of each real-time PCR run, the data were automatically analyzed by the system and amplification plots were obtained. FIG. 6 shows the amplification plots of the five transcripts. All five curves group together and emerge up at cycle 15. The copy numbers of the five transcripts determined by this quantitative assay turned out to be $9.6 \times 10^3$ (0 mismatches), $1.1 \times 10^4$ (2 mismatches), $7.2 \times 10^3$ (3 mismatches), $5.6 \times 10^3$ (4 mismatches) and $6.3 \times 10^3$ (5 mismatches); these copy numbers were very close to the expected $8 \times 10^3$. In the $\log_{10}$ scale, the highest difference among these five determined copy numbers was 0.29 $\log_{10}$. Thus, the partially double-stranded linear probe set quantified transcripts with up to five mutations as accurately as the wild type (0 mismatches). This demonstrates the tolerance of partially double-stranded probes to mismatches and demonstrates their utility for quantifying target regions containing genetic polymorphisms.

The invention claimed is:

1. A composition comprising a pair of labeled nucleotide sequences, the first member of the pair being selected from the group consisting of [SEQ ID NO: 6] and [SEQ ID NO: 7], and; the second member of the pair comprises [SEQ ID NO: 11].

2. The composition of claim 1, wherein the first member of the pair is labeled with a fluorescent label and the second member of the pair is labeled with a quencher.

3. The composition of claim 1, wherein the first member of the pair is labeled with a quencher and the second member of the pair is labeled with a fluorescent label.

4. The composition of claim 1, wherein the pair of labeled nucleotide sequences comprises [SEQ ID NO: 6] and [SEQ ID NO: 11].

5. The composition of claim 4, wherein the one member of the labeled pair of nucleotide sequences is labeled with a fluorescent label and the other member of the labeled pair of nucleotide sequences is labeled with a quencher.

6. The composition of claim 1, wherein the pair of labeled nucleotide sequences comprises [SEQ ID NO: 7] and [SEQ ID NO: 11].

7. The composition of claim 6, wherein the one member of the labeled pair of nucleotide sequences is labeled with a fluorescent label and the other member of the labeled pair of nucleotide sequences is labeled with a quencher.

8. A composition comprising a labeled nucleotide sequence, wherein the label is a quencher and the nucleotide sequence comprises [SEQ ID NO: 11].

\* \* \* \* \*